(12) United States Patent
Cooper et al.

(10) Patent No.: US 12,127,852 B2
(45) Date of Patent: Oct. 29, 2024

(54) FITNESS SYSTEMS AND METHODS

(71) Applicant: Cooper Health And Fitness Applications, LLC, Dallas, TX (US)

(72) Inventors: Tyler Clark Cooper, Dallas, TX (US); Terdema Ussery, III, Dallas, TX (US)

(73) Assignee: Cooper Health And Fitness Applications, LLC, Dallas, TX (US)

( * ) Notice: Subject to any disclaimer, the term of this patent is extended or adjusted under 35 U.S.C. 154(b) by 0 days.

(21) Appl. No.: 18/520,152

(22) Filed: Nov. 27, 2023

(65) Prior Publication Data

US 2024/0099655 A1 Mar. 28, 2024

Related U.S. Application Data

(63) Continuation of application No. 16/908,724, filed on Jun. 22, 2020, now Pat. No. 11,844,626, which is a continuation of application No. 16/556,113, filed on Aug. 29, 2019, now Pat. No. 10,722,172, which is a continuation of application No. 16/164,096, filed on Oct. 18, 2018, now Pat. No. 10,413,238.

(51) Int. Cl.
| | |
|---|---|
| *A61B 5/00* | (2006.01) |
| *A61B 5/0205* | (2006.01) |
| *A61B 5/024* | (2006.01) |
| *A61B 5/083* | (2006.01) |
| *A61B 5/091* | (2006.01) |
| *A61B 5/11* | (2006.01) |
| *A63B 24/00* | (2006.01) |

(52) U.S. Cl.
CPC .......... *A61B 5/4884* (2013.01); *A61B 5/0022* (2013.01); *A61B 5/0205* (2013.01); *A61B 5/681* (2013.01); *A61B 5/02438* (2013.01); *A61B 5/0833* (2013.01); *A61B 5/091* (2013.01); *A61B 5/1112* (2013.01); *A61B 2560/0475* (2013.01); *A63B 2024/0065* (2013.01)

(58) Field of Classification Search
CPC ... A61B 5/1118; A61B 5/0205; A61B 5/0022; A61B 5/0833; A61B 5/02438; G06F 1/163; G09B 19/00
See application file for complete search history.

(56) References Cited

U.S. PATENT DOCUMENTS

| | | | |
|---|---|---|---|
| 9,237,868 | B2 | 1/2016 | Seppanen et al. |
| 9,662,538 | B2 | 5/2017 | Meek et al. |
| 9,737,761 | B1 | 8/2017 | Sivaraj |
| 10,413,238 | B1 | 9/2019 | Cooper et al. |
| 2012/0191469 | A1 | 7/2012 | Akradi |
| 2014/0135592 | A1 | 5/2014 | Ohnemus et al. |

(Continued)

OTHER PUBLICATIONS

Henar Martfn et al., "Enhancing Activity Recognition by Fusing Inertial and Biometric Information," IEEE, 2011 (8 pages).

*Primary Examiner* — Kesha Frisby
(74) *Attorney, Agent, or Firm* — Fox Rothschild LLP

(57) ABSTRACT

The invention is directed to systems and methods that can determine a user's fitness based on a single factor such as oxygen lung volume (pmVO2). A heart rate measurement is conducted on the user after the user performs a physical test specified by a fitness application of the system. The heart rate measurement is converted into a pmVO2 value and compared to pmVO2 values of other individuals. The system assigns the user a fitness grade based on the comparison result. The system further includes an artificial intelligent system that helps the user to move from a grade to a higher grade.

20 Claims, 12 Drawing Sheets

(56) References Cited

U.S. PATENT DOCUMENTS

| | | |
|---|---|---|
| 2017/0136298 A1 | 5/2017 | Bae et al. |
| 2017/0143262 A1 | 5/2017 | Kurunmäki et al. |
| 2017/0273619 A1 | 9/2017 | Alvarado et al. |
| 2017/0282011 A1 | 10/2017 | Jang et al. |
| 2017/0300655 A1 | 10/2017 | Lane et al. |
| 2017/0345332 A1 | 11/2017 | Obay |

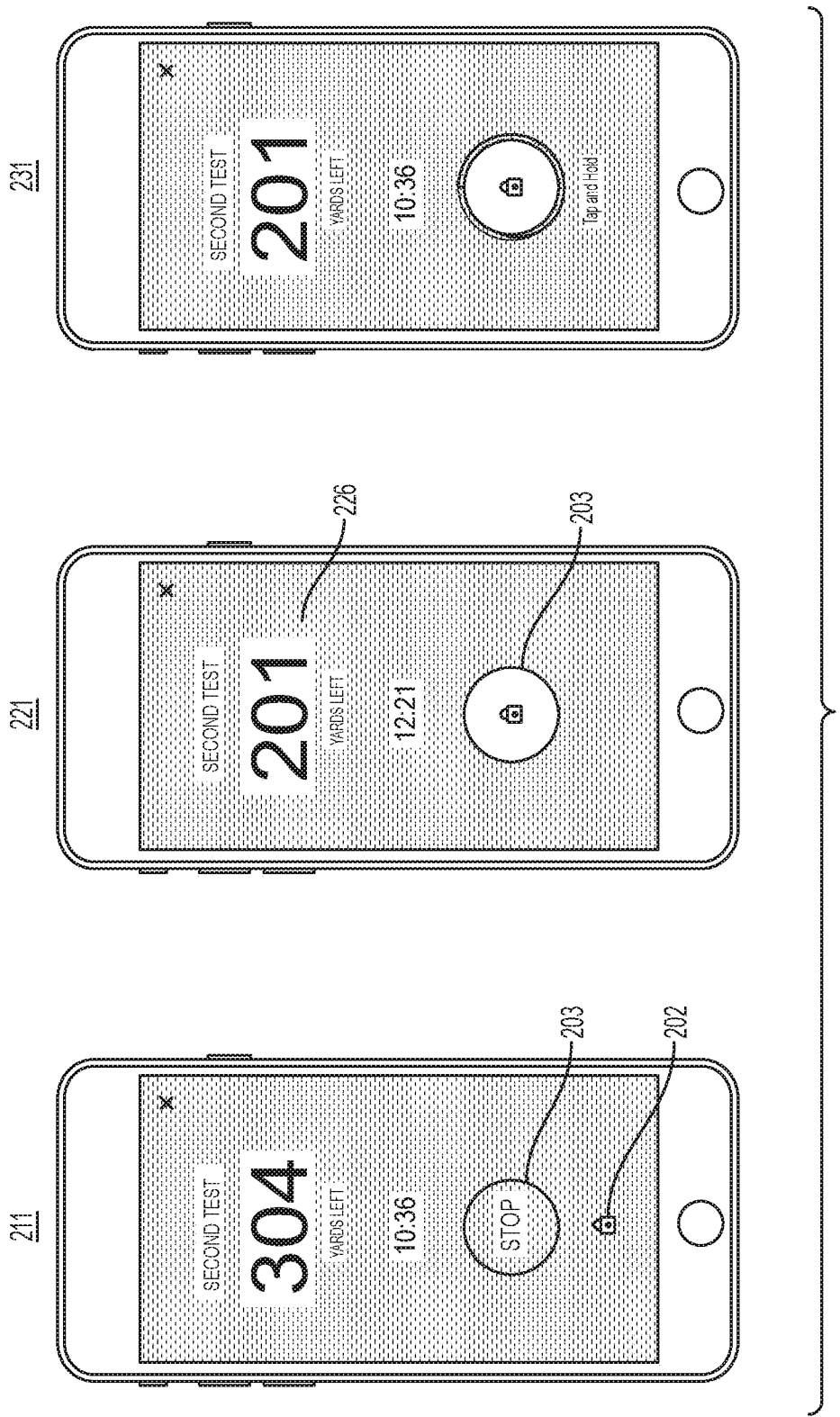

FITNESS SYSTEMS AND METHODS

CROSS REFERENCE TO RELATED APPLICATIONS

This application is a continuation of and claims priority to US. Non-provisional application Ser. No. 16/908,724, filed on Jun. 22, 2020, which is a continuation of and claims priority to U.S. Non-provisional application Ser. No. 16/556,113, filed on Aug. 29, 2019, now U.S. Pat. No. 10,722,172, which is a continuation of and claims priority to U.S. Non-provisional application Ser. No. 16/164,096, filed on Oct. 18, 2018, now U.S. Pat. No. 10,413,238. The entire contents of these patent applications are herein incorporated by reference.

FIELD OF THE INVENTION

The present invention is related to improvements in fitness systems.

BACKGROUND OF THE INVENTION

The existing fitness or health systems dry not provide an accurate measurement of fitness in a standardized and verifiable way. Exercise type measurements such as the number of push up or the time it takes to run a distance provide certain evidence of fitness, but there is no overall measure fitness or biometric fitness, and none is accurate or verifiable. Physiological or overall determination of fitness can be complex and could involve many different factors. Most of the fitness systems also do not incorporate fitness in the set of medical diagnostics and patient evaluation. Known existing systems have other deficiencies such as being too complex, involving too great a startup effort, and being unable to actually affect fitness by way of its implementation in a practical sense. Existing systems require knowing a multitude of factors from the user, such as drinking, smoking, and eating habits, family medical history, filling out questionnaire etc. in order to make a fitness determination. Other deficiencies relate to the was or mechanism in which the software or system interacts with the users. Such systems can, for example, rely on in-app communications of performance data or status which can create engagement hurdles and isolated silos of interaction or communications. Another potential deficiency in existing system relates to the lack of integration of and management of a group of individuals. Existing system an known to focus on individuals and lack broader integration such as at a company level. Accordingly, there is a need for an improved fitness or health system that addresses at least some of the above problems. There are also other deficiencies that can be remedied based on illustrative descriptions provided herein.

SUMMARY OF THE INVENTION

In accordance with principles of the invention, a system for determining physical fitness is contemplated. In one embodiment, the system comprises a device wearable by a user having a sensor configured to conduct a physical measurement of the user. The system also comprises a mobile device including a transceiver configured to receive a physical measurement via a first communications network and transmit data via a second communications network, a geographical position calculating device configured to measure a distance traveled by the user, a timer configured to set a period of time, and a fitness application: The fitness application configures the mobile device to receive a physical measurement from the wearable device and provide options via a user interface to select one or more physical tests to be performed by the user. In response to a selection of the test, the fitness application instructs the mobile device to measure, via the geographical position calculating device, the distance traveled by the user during the performance of the test, measure, via the timer, the time spent by the user during the performance of the test, instruct the wearable device to conduct a physical measurement, and transmit a predicted long oxygen volume max (pmVO2) or information representative of pmVO2 of the user from the physical test administered by the fitness application to another system.

In one embodiment, the system further comprises a management computer system that included a database and a central subsystem. The database is configured to store health information of a plurality of individuals and a fitness scale. The health information includes pmVO2s of the individuals and health conditions associated with their pmVO2s and the fitness scale includes multiple grades for classifying the user. The central subsystem is configured to assign a threshold pmVO2 to each grade based on the health information, analyze the pmVO2 or information representative of pmVO2 received from the mobile device in view of the pmVO2 and health information stored in the database, and determine a grade from the fitness scale to classify the user based on the analysis.

The management system is configured to receive a roster of individuals from an enterprise computer. The individuals on the roster are users of the wearable device and the mobile deice and authorized users of the fitness application. The management system is also configured to verify that persons attempting to user the fitness application are authorized users can the roster. The management system is further configured to collect and aggregate the pmVO2 or information representative of pmVO2 of the one or more authorized users in the database and remove information identifying the one or more authorized users so that the pmVO2 or information representative of pmVO2 is saved in the database anonymously. Additionally, the management system is configured to determine a grade using the collected pmVO2 or information representative of pmVO2 and the fitness scale to classify the one or more authorized users.

In another embodiment, the system further comprises a management computer system that includes a database, a central subsystem, and an artificial intelligence (AI) subsystem. The database is configured to store health information of a plurality of individuals and a fitness scale. The health information includes pmVO2s of the individuals and health conditions associated with their pmVO2s and the fitness scale includes multiple grades for classifying the user. The central subsystem is configured to assign a threshold pmVO2 to each grade based on the health information, analyze the pmVO2 or information representative of pmVO2 received from the mobile device in view of the pmVO2s and health information stored in the database, and determine a grade from the fitness scale to classify the user based on the analysis. The AI subsystem is configured to communicate suggestions via a chatbot that generates natural language messages using the database and the central subsystem. The suggestions include action items to be completed by the user that can move the user from the determined grade to a higher grade.

The management system is configured to receive a roster of individuals from a computer. The computer may be an enterprise computer of an entity that employs the individuals (employees), a hospital or clinic that provides medical and surgical treatment to the individuals (nations), government that conducts medical testing on the individuals, an insurance company that screens the individuals (e.g., life or health insurance candidates) or has accepted the individuals (e.g., life; or health insurance members), or other entities that are made up with other individuals or groups. The individuals can be other group of people and be associated with other entities via other relationships. The individuals are users of the wearable device and the mobile device. The management system is further configured to identify a subset of users that have a fitness grade in the fitness scale that impacts a predicted healthiness of the individuals in the roster as whole and transmit a message containing an alert to the enterprise computer. The management system is further configured to generate and transmit my sages containing suggestions provided by the AI subsystem to the mobile devices of the subset of users via the chatbot. The management system is further configured to control the operation of the AI subsystem, chatbot and related generation and transmission of the messages to be directed substantially only to the subset of users relative to the other users from that entity. The management vent system is further configured to monitor level of activity and fitness grades of the subset of users via the chatbot and finless application after transmitting the messages containing the suggestions and use the monitored information in the AI subsystem in responding to an individual user's monitored activity and generating new messages by the chatbot. The management system is further configured to reclassify one or more users in the subset of users that have a new fitness grade that impacts the predicted healthiness to a higher fitness grade based on the monitored activity and fitness grades and remove the one OT more reclassified users from the subset.

In one embodiment, the chatbot is configured to communicate with the users without requiring the user to open the fitness application or have it running on the mobile device.

In one embodiment, the one or more physical tests include a first physical test requiring the user to travel in a period of time and the total distance traveled by the user in the determined period of time is measured by the geographical position calculating device.

In one embodiment, the fitness application is configured to instruct the wearable device to conduct and transmit the measurement upon expiration of the determined period of time.

In another embodiment, the one or more physical tests include a second physical test requiring the user to travel a distance determined by the fitness application and the total time spent by the user to complete the determined distance is measured by the timer.

In another embodiment, the fitness application is configured to instruct the wearable device to conduct and transmit the measurement upon completion of the determined distance.

Counterpart method and commuter-readable medium embodiments would be understood front the above and the overall disclosure. Also, broader, narrower, or different combinations of the described features are contemplated, such that, for example features can be removed or added in a broadening or narrowing way.

In some embodiments, the management system (and the fitness application) is configured to be accessible and usable by other individuals beyond those on the roster. For example, a mobile device user from the general public can download the fitness application from an app store (e.g., Google Play Store or Apple App Store), create his own login credentials, and use the fitness application as he wishes to improve his fitness level or other purposes, even though the user is not on the roster or is not related to the entity that uses the management system. The user's fitness level can be compared to his previous measured fitness levels, fitness levels of other users in the general public, fitness levels of the individuals on a rosier, or other fitness levels toted in the management system.

BRIEF DESCRIPTION OF THE DRAWINGS

Various features of examples in accordance with the principles described herein may be more readily understood with reference to the following detailed description taken in conjunction with the accompanying, drawings, where litre reference numerals is designate like structural elements, and in which:

FIGS. 2A-2H depict an illustrative fitness application and an illustrative flow process of the fitness application in accordance with some embodiments of the invention;

DETAIL DESCRIPTION OF THE INVENTION

Figure 1:
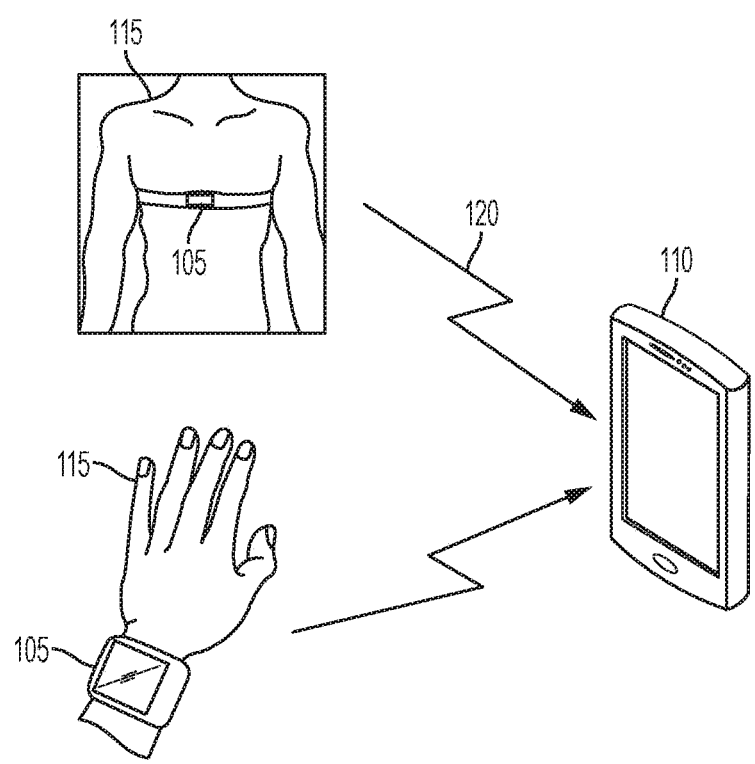
FIG. 1 depicts illustrative devices of a system for determining physical fitness in in accordance with some embodiments of the present invention.

FIG. 1 depicts illustrative devices 105, 110 of a system for determining physical fitness (or biometric fitness) in accordance with some embodiments of the present invention. Reference number 111 represents a wearable device whereas reference number 110 represents a mobile device such as a mobile wireless (cellular) telephone. The wearable device 105 may be a wrist-worn device (e.g., a device provided in a shape of a watch or bracelet), a neck-worn device (e.g., a device provided in a shape of a necklace), a chest-worn device (e.g., a device provided a shape of a chest strap), and other devices provided in various shapes that may be worn or otherwise attached to the user 115. The wearable device 105 may also be an implant device. The wearable device 105 may include a sensor and a transmitter.

The sensor is configured to conduct a physical measurement of the user. Preferably, the physical measurement includes or is a heart rate measurement. The sensor can conduct a heart rate measurement by detecting bean contraction through the user's skin (heart contraction generates a signal that can be picked up by the sensor through the skin). The wearable device 105 can be worn by the user with the sensor positioned on or near the user's heart. The wearable device 105 can also be worn by the user with the sensor positioned on a body location remote from the user's heart when an activity correlating to heart contraction can be sensed, such as the user's veins or pulsing of the user's veins. The sensor can conduct a heart rate measurement by detecting light scattered or absorbed in the blood streams that varies with heartbeat. The sensor can also conduct a bean rate measurement in other manners. The wearable device 105 may be a Bluetooth Low Energy (BLE) device or a smart electronic device (i.e., electronic device having a microcontroller and/or can perform functions other than physical measurements). For example, a chest-worn device may be a BLE device that is configured to solely conduct a bean rate measurement. For example, a wrist-worn device may be a smart electronic device such as a smart watch that can make phone calls in addition to conducting physical measurements.

The transmitter is configured to interface with the network 120 and transmit physical measurements to the mobile device 110. The transmitter supports communications protocols (for wireless connections) and communications wires described below (for wired connections). The physical measurement being transmitted may include or be a heart rate measurement. The transmitter may be a standalone device or part of a transceiver in the wearable device 105.

The sensor and transmitter may be configured to conduct and transmit other physical measurements, respectively, in addition to the heart rate measurement. The sensor and transmitter may also be configured to conduct and transmit only the heart rate measurement, respectively. A combination thereof is also contemplated. For example, the sensor may be capable of conducting several types of physical measurements (e.g., body temperature) and the transmitter may be configured to transmit only the heart rate measurement from the several physical measurements to the mobile device. For example, the sensor may be capable of zanily conducting heart rate measurements and the transmitter may be configured to transmit the bean rate measurement from the sensor and other physical measurements from other devices to the mobile device.

The wearable device 105 end the mobile device 110 communicate with each other via a network 120. The network 120 may be established through a wireless or wired connection. A wireless network may established by a communications protocol such as Wi-Fi, 802.11. Bluetooth, radio frequency systems such as 900 MHz, 1.4 GHz, and 5.6 GHz communication systems, infrared, GSM, GSM plus EDGE, CDMA, quadband, and other cellular protocols, VOIP, ZigBee, near field communication, or any other suitable protocol. A wired network may be established by a USB cable (e.g., MicroUSB, USC-C, etc.), an optical fiber, Ethernet cable, or other types of wires.

The mobile device 110 includes a receiver configured to receive a physical measurement from the wearable device 105 via the network 120. The receiver supports communications protocols (tor wireless connections) and communications wires described above (for wired connections). The received may be a standalone device or part of a transceiver in the mobile device 110. The mobile device 110 may be a mobile computer, a tablet computer, a cellular device, a smartphone, a personal digital assistant (PDA), a near-field communication device, or other equivalent competing devices. In some embodiments, the mobile device 110 may be substituted with or the system for determining physical fitness may further include a desktop computer or other immobile computer devices that include the above electronic components and functions.

The system for determining physical fitness also includes a geographical position calculating device (e.g., GPS device) configured to determine the location of user and the distance the user has traveled from one point to another point. The system for determining physical fitness also include timer configured to measure time intervals, such as measuring the amount of time elapsed from a particular time when the timer is activated to the time when the timer is deactivated activating at 12:00 pm or 0 second and deactivating at 12:01 pm or 60 seconds later) and counting down from a specified time interval (e.g., counting from 60 seconds to 0 second). The mobile device 110 may include the geographical position calculating device and the timer. The geographical position calculating device and the timer may also be in other parts of the system for determining physical fitness such as the wearable de ice 104 or be separate devices from the mobile device 110 and the wearable device 105. The fitness application described below may include computer algorithms that allow the fitness application to utilize the geographical position calculating device and the timer to perform its function. The fitness application may also be implemented to have its own geographical position calculating software and timer software. The fitness application may also be configured to operate based on a combination of sack hardware and software.

FIGS. 2A-2H depict an illustrative fitness application and an illustrative flow process of the fitness application in accordance with some embodiments of the invention. The fitness application is installed on the mobile device 110. The fitness application may be one that is pre-installed on the mobile device during manufacture and assembly or that is subsequently installed on the mobile device by the user or other individual. The fitness application can be Android or iOS-based, or be based on other operating systems. The fitness application is configured to assess a fitness level of the user and the assessment process includes requesting the user to perform a physical test provided by the fitness system and conducting a physical measurement of the user before, during, and/or after performance of the test. Preferably, the physical measurement is a heart rate measurement. The fitness application and the mobile device communicate with the wearable device to control and receive the measurement.

Figure 2A:
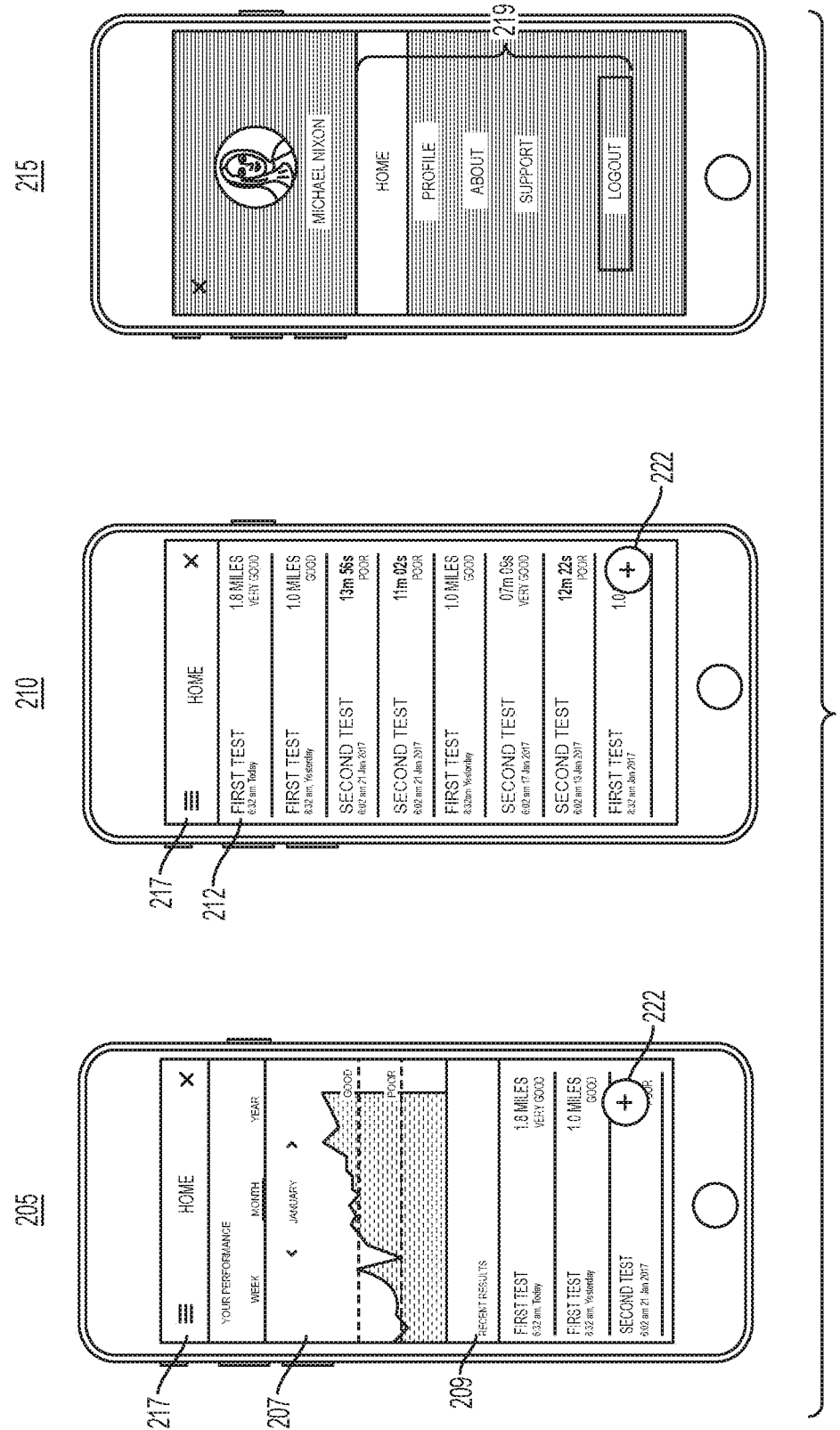

After loading the fitness application, a homepage or main screen is presented to the user. FIG. 2A depicts an illustrative homepage showing an overview of the user's performance 207 and previous test results 209 (step 205). Upon selecting an area in the previous test results 209, the fitness application provides a list 212 of activities previously performed by the user (step 210). It should be understood that, in this and other figures, each displayed screen May be a graphical user interface (GUI) that includes one or more commands (e.g., digital or built-in buttons) allowing the user to interact with the fitness application. For example, although a GUI or command is not expressly mentioned with respect to the user's performance 207 and previous test results 209, one with ordinary skill the art would understand that each displayed information is part of a GUI and includes one or more commands. The GUI or commands permit the user to select an area in displayed information to instruct the fitness application to further display the associated information err portion additional functions. The list 212 is sorted chronologically with the latest activity first. The fitness application includes a navigation menu command 217 that can display one or more additional commands 219 upon selection (step 215). The additional commands 219 include a home command, a user profile command, an about command, a support command, and a logout command. The user profile command may be configured to allow the user to input and save his or her weight and other information (e.g., height, gender, age, etc.) in the fitness application.

Figure 2B:
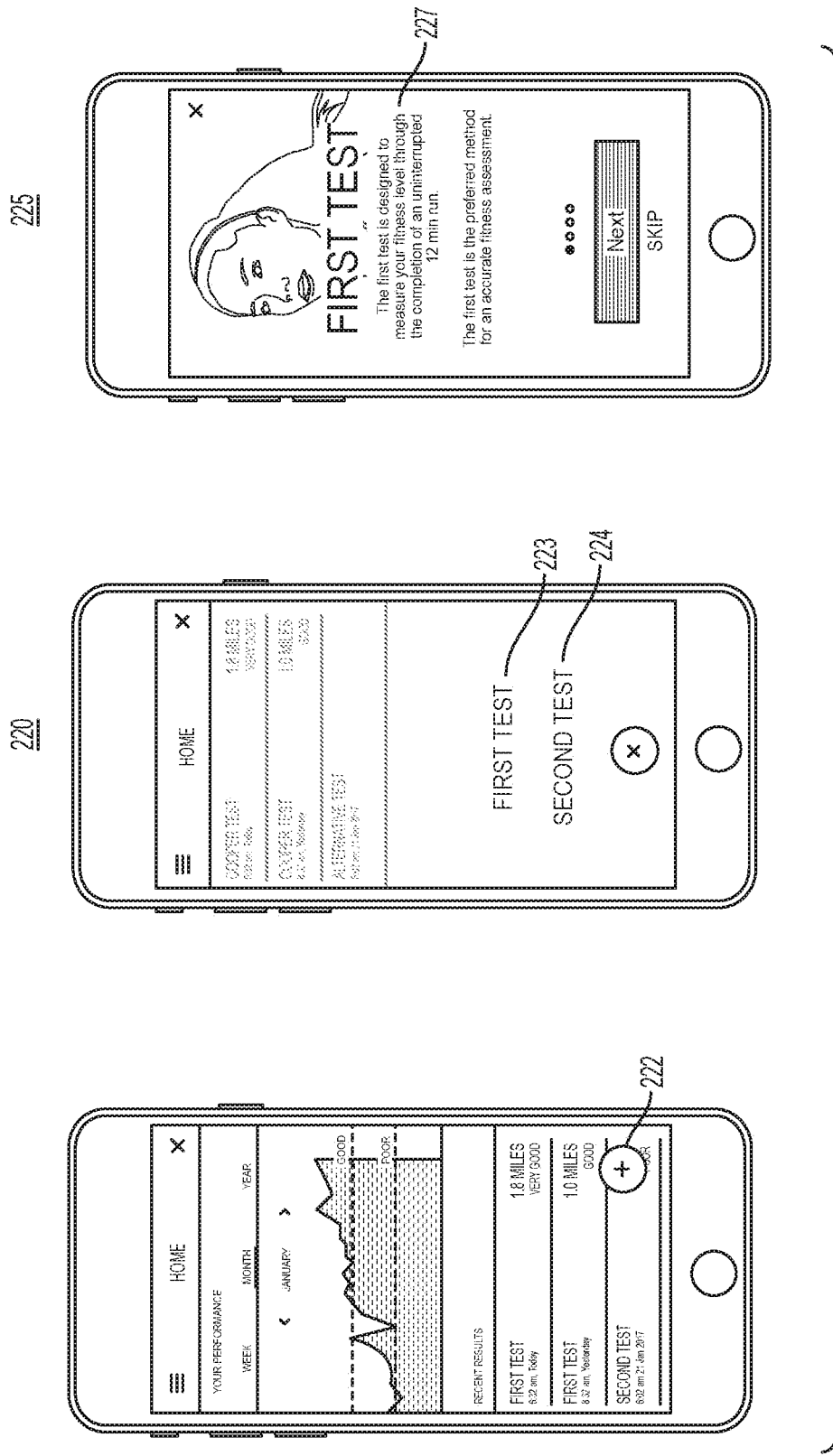

The homepage also includes a test command 222. After selecting the test command 222, the fitness application displays a first test command 223 and a second test command 224 as shown in FIG. 2B asking to the user to select one of the test command, anti perform a physical test prescribed by the selected test command. The first test command 223 instructs the user to exercise for a period of time (time-based exercise or fixed-time exercise). The exercise is preferably running or walking. The exercise is also preferably one that requires the user to perform the exercise in an uninterrupted or continuous manner for a period of time. The period of time is determined by and preprogrammed into the fitness application. In some embodiments, the period of time may be determined and set by the user. The amount of exercise completed in the period of time, such as how far the user has run or walked, is also measured by the fitness application. The fitness application operates in conjunction with the timer to set and count from a time interval. The fitness application operates in conjunction with the geographical position calculating device to measure the distance the user has run or walked. In some embodiments, the exercise may be push-ups, sit-ups, jumping jacks, and other activities, and the timer and geographical position calculating device may or may not need to be utilized.

Figure 2C:
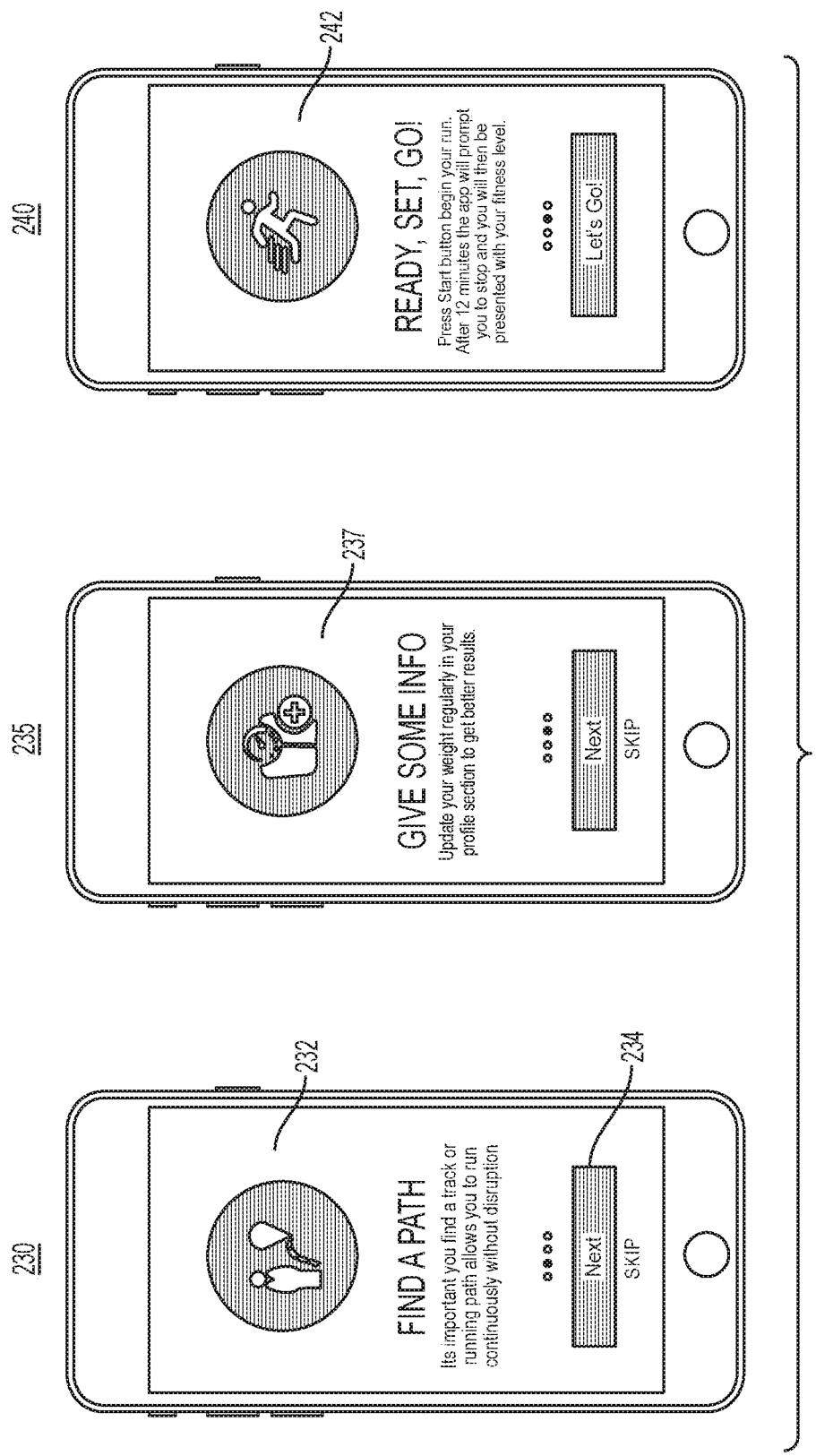
Figure 2D:
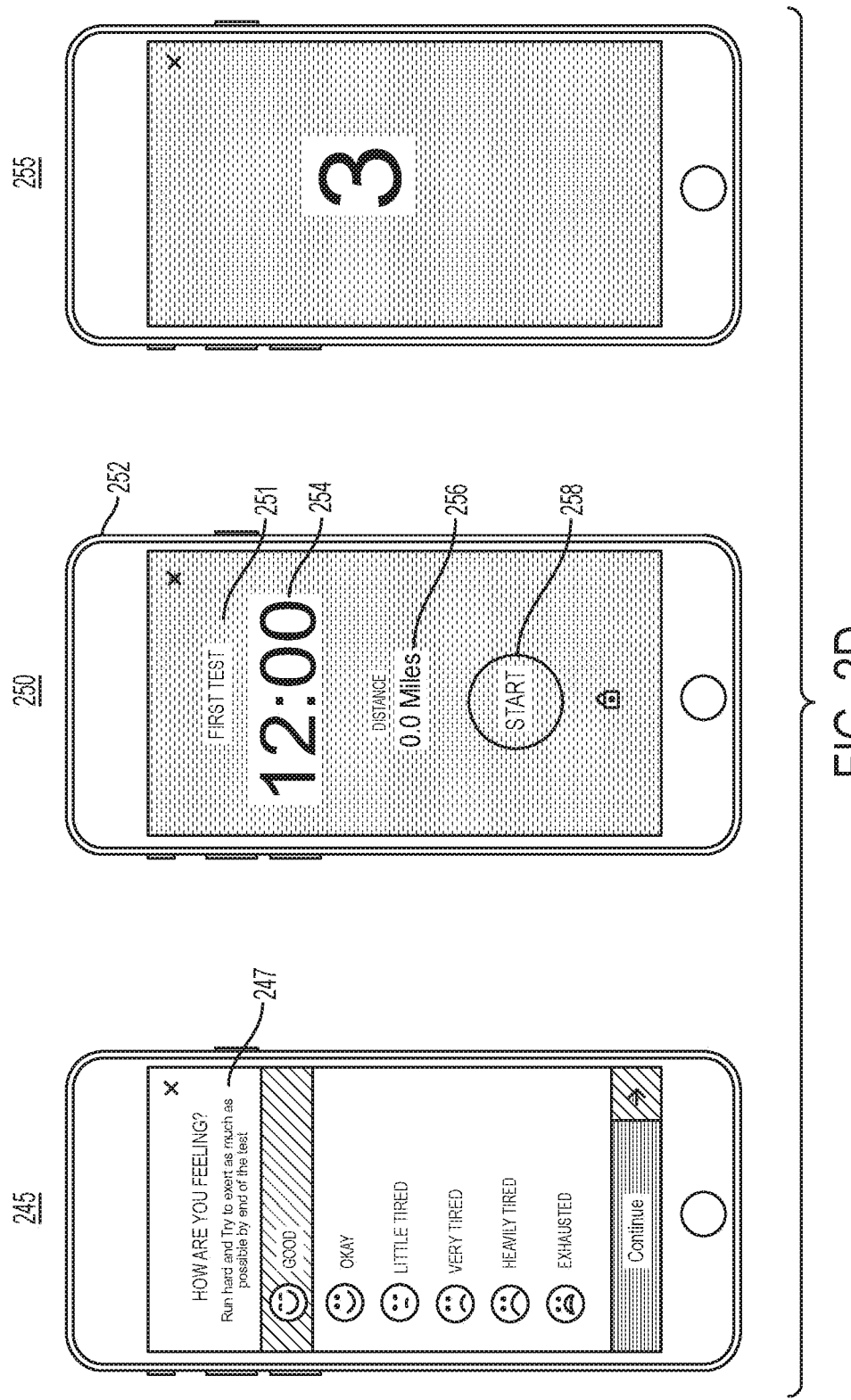

For example, upon selecting the first test command 223, the fitness application may provide exercise instructions to prepare the user for the first physical test as shown in FIGS. 2B-2C. The exercise instructions may include a first screen 227 describing what the first exercise is such as completing an interrupted 12 minute run (step 225). The exercise instructions may include a second screen 232 instructing the user to find a track or running path that allows him or her to run continuously without disruption (step 230). The exercise instructions may include a third SUMO 237 asking the user to input or update his or her weight via the user profile command (step 235). The exercise instructions may include a fourth screen 242 informing the user to press the start command and begin the run and that the user's fitness level will be determined at the conclusion of the run (step 240). Each screen may include a skip command 234 allowing the user to skip any of the instructions or screen or to reach the exertion level capture screen 247 directly.

Referring to FIG. 211 the exercise instructions may include an exertion level capture screen 247 allowing the user to select an exertion level that describes the users current exertion level or the user's exertion level before he or she begins the exercise (step 245). The exertion level represents how tired the user is. The capture screen 247 may include multiple exertion levels for selection such as a first level or good (i.e., having abundant of energy and not tired), a second level or okay (i.e., not tired), a third level or little tired, a fourth level or very tired (i.e., more tired than the third level), a fifth level or heavily tired (i.e., more tired than the fourth level), and a sixth level or exhausted (i.e., more tired than the fifth level or the most using level that can be selected). After receiving the exertion level information, the fitness application displays the selected first physical test 252, the time period 254 that the user is required to run continuously, an odometer 256 tracking the distance the user has run, and a start command 258 to begin the exercise in a test screen 251 (step 250). Upon selecting the start command 258, the fitness application may initiate and display a countdown such as a 3-second countdown to help the user prepare his or her pace (step 255). The fitness application may notify the user once the countdown is over such as by sound and/or vibration. The fitness application then executes the functions associated with the first physical test after the countdown. Through the timer, the fitness application specifies a predetermined time interval to (e.g., 12 minute) and counts down from the specified time interval until the time interval reaches zero second. Through the geographical position calculating device, the fitness application measures the distance that the user has traveled and outputs the measured distance via the odometer in real-time.

Figure 2E:
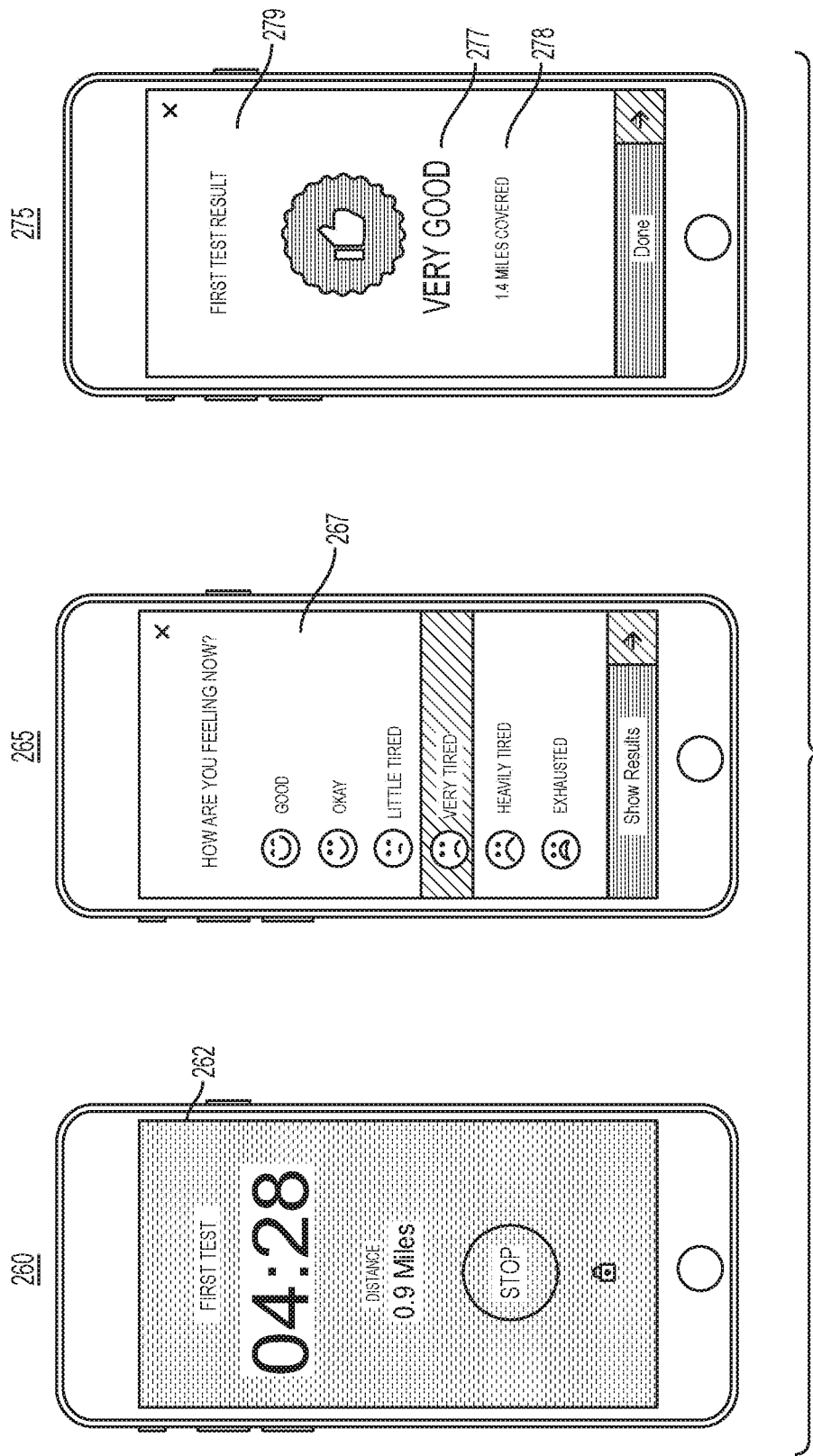

Referring to FIG. 2E, the fitness application updates the screen in step 250 to display the countdown information from the timer and the distance information from the geographical position calculating device in real-time (step 260). The test progress screen 262 can show the amount of time that remains in the predetermined time interval (e.g., 4 minutes and 28 seconds) and the distance the user has run until that particular time from the starting time (e.g., 0.9 miles). The test progress screen 262 can also include a stop command allowing the user to stop or cancel the test at any point of time. The stop command can further direct the user to the homepage or any other screen that appears before or after step 255. Upon completing the test or expiration of the time interval, the fitness application presents a second exertion level capture screen 267 that is identical or similar to the first exertion level capture screen 247 for user's selection (step 265). The fitness application may notify the user once the test is completed or the time interval expires such as by sound and/or vibration.

Figure 2F:
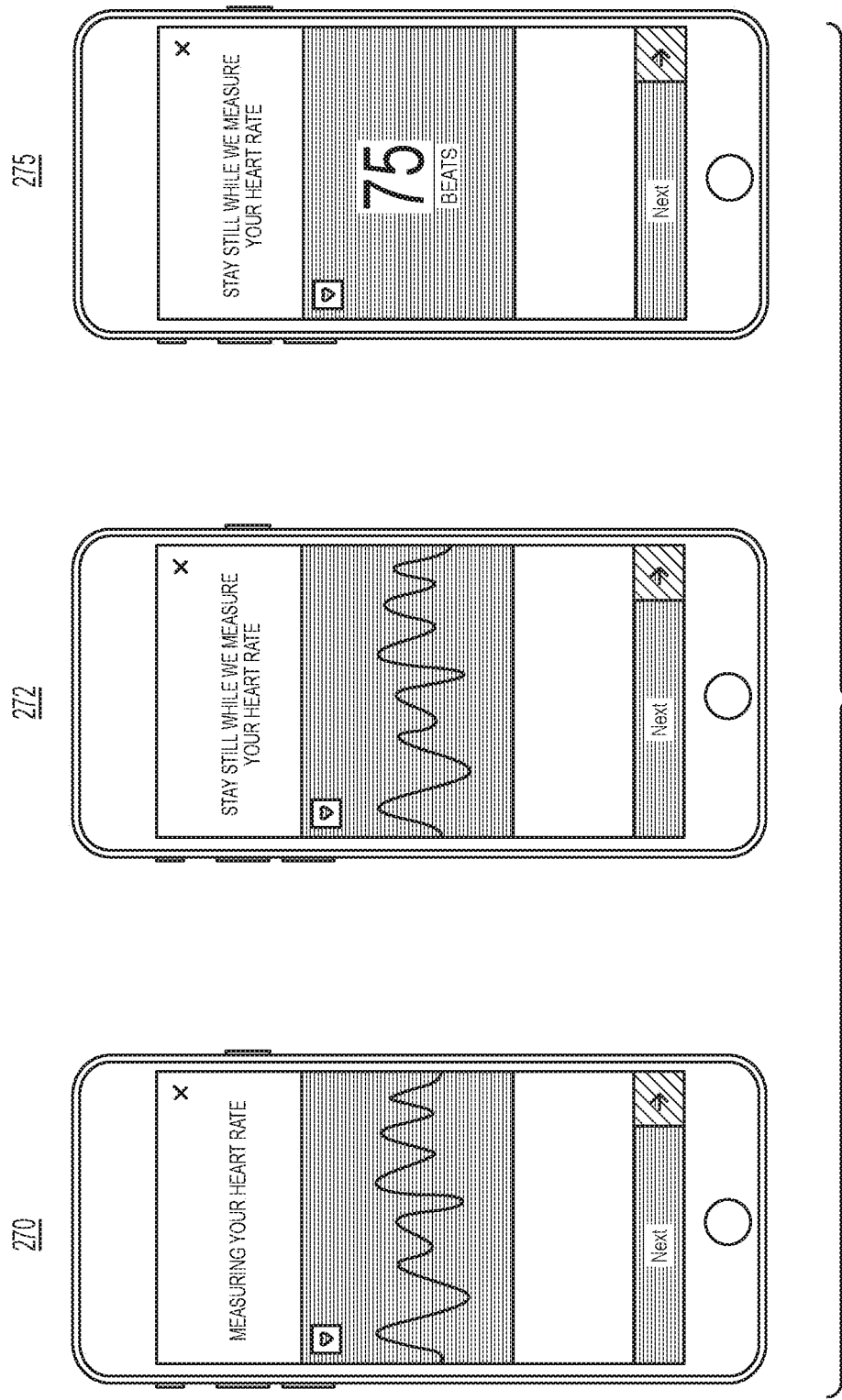

FIG. 2F illustrates the fitness application measuring the user's heart rate. The measurement 271) can occur before, during, and/or after performance of the test (e.g., at step 250, 290, and/or 265 respectively). The measurement. 270 can also occur at any other time or step or between two steps (e.g., between after completion of step 260 and before step 265. The fitness application can communicate with the wearable device (via the mobile device) to conduct and receive a measurement. The sensor in the wearable device can be configured to constantly measure heart beat or to measure heart beat only when instructed by the fitness application (via the mobile device). After the measurement is obtained, it is transmitted to the fitness application (via the mobile device) and is displayed to the user (step 275). The fitness application can provide suggestions or warnings if the senor cannot conduct a measurement or the fitness application cannot receive the measurement, such as asking the user to stand still (step 272). The fitness application can also provide suggestions or warnings if the user did not properly or completely perform the test. The received heart rate is then used by the fitness application to determine the predicted coax lung oxygen volume or predicted VO2 max. Predicted VO2 max is also known as predicted maximal oxygen consumption, predicted maximal oxygen uptake, or predicted peak oxygen uptake. For simplicity and convenience, predicted VO2 max is referenced herein using the terra pmVO2 which stands for predicted maximal VO2. pmVO2 may be the only information determined from the received heart rate (i.e., the received heart rate is not used to determine any other information except pmVO2). The fitness application includes such computer algorithms. pmVO2 can be determined in some instances without using the user's heart rate measurement. The pmVO2 value is then applied to an archive of health information for a large set of individuals to assess a fitness level of the user. This can be done if desired by saving a fitness scale in the mobile device (in the mobile application) and comparing the measurement to the scale. In some embodiments, the assessment may further consider the user's weight entered in screen 237, the type of exercise selected (first or second test), the exertion level selected in the first capture screen 247, the exertion level selected in the second capture screen 272, the total distance the user has run in the predetermined time interval, the predetermined time interval, or a combination thereof to determine the fitness level. The fitness level assessment and other relevant system, databases, and components are described in more detail later in the application. The determined fitness level 277 and results of performing the first physical test 278 are shown in a result screen 279 (stems 275). The fitness application can further provide tips to improve the results 278.

pmVO2 is different from actual VO2 max in that pmVO2 is determined based on computer algorithms written to calculate such a number using time and distance (e.g., the required time and the distance the user has run in the given time, and the required distance and the amount of time the user spent in completing the required distance), whereas actual VO2 max is a value determined by using a metabolic cart and a treadmill, or similar equipment in some embodiments, the determination of pmVO2 may further consider heart rate measurement by the wearable device.

In one embodiment, the first test is a running diagnostic test. The test requires the user to run for a predetermined period of time. The user's heart rate may be subsequently measured by the wearable device after the running diagnostic test. The user's heart rate may, be also be measured before the running diagnostic test. The determination of pmVO2 via the running diagnostic test does not require the user's heart rate before and after the running diagnostic test, but the user's heart rate before and after the running diagnostic test may be saved in the fitness application. The user's weight may also be collected before, during and/or after the running diagnostic test but is not required for the determination of pmVO2. The user's age and gender may also be collected and may or may not be considered in the determination of pmVO2.

As discussed earlier, the fitness application also provides a second test command 224 as shown in FIG. 213. The second test command instructs the user to travel a distance (distance-based exercise or fixed-distance exercise). This exercise is also preferably one that requires the user to travel a distance in an uninterrupted or continuous manner. The distance is determined by and preprogrammed into the fitness application In some embodiments, the distance may be determined and set by the user. The amount of time spent by the user to complete the distance is also measured by the fitness application. The fitness application operates in conjunction with the geographical position calculating device to set the predetermined distance and measure the distance the user has traveled. The fitness application operates in conjunction with the timer to measure the time the user has spent. The term travel can refer to running, walking, or other kg and foot movement. In some embodiments, the second test command and the fitness application may be configured to accommodate other exercises such as push-ups, sit-ups, jumping jacks, and other activities and instruct the user to perform a number of actions or movements (e.g., 50 push ups, sit-ups, or jumping jacks). The timer and geographical position calculating device may or may not need to be utilized for these exercises.

Figure 2G:
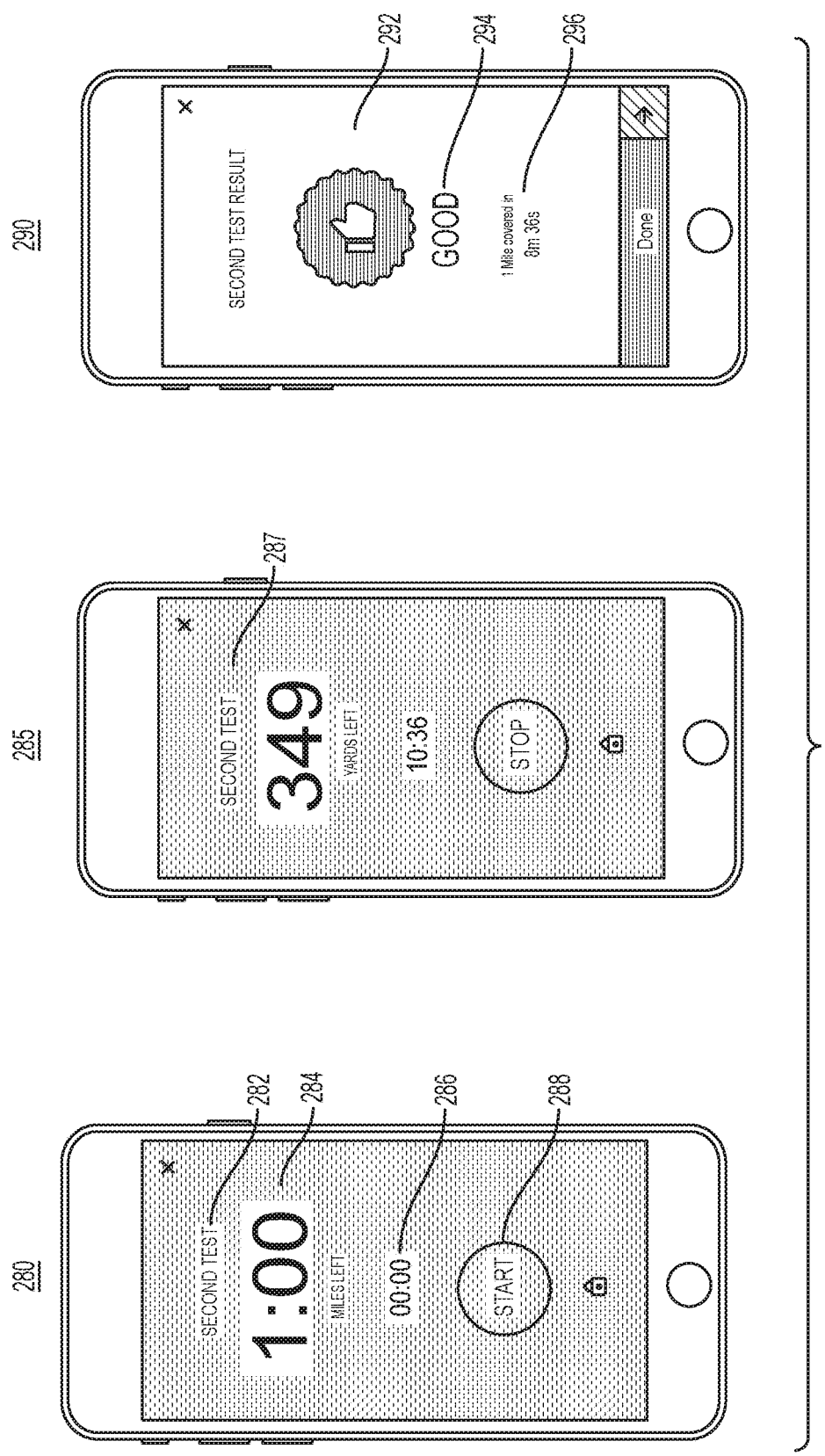

For example, upon selecting the second test command 224, the fitness application may provide a screen shown in FIG. 2G (step 280). The screen displays the selected second physical test 282, the distance 284 that the user is required to travel continuously (or the number of push-ups, sit-ups, jumping jacks, or other activities that the user is required to perform), a clock 286 tracking the time the use has spent, and a start command 288 to begin the exercise. Upon selecting the start command 288, the fitness application executes the functions associated with the second physical test. Through the geographical position calculating device, the fitness application specifies a predetermined distance (e.g., 1 mile) and measures the distance the user has traveled or the remaining distance that the user needs to travel. The distance is measured and displayed in area 284 in real-mime. Through the timer, the fitness application operates in conjunction with the timer to measure the time the user has spent.

The fitness application updates the screen in step 280 to display the distance information from the geographical position calculating device in real-time and the countdown information from the timer (step 285). The test prowess screen 287 can show the distance that remains in the predetermined distance (e.g., 349 yards left) and the time the user has spent to run from the starting location to that distance (e.g., 10 minutes and 35 seconds for running 1411 yards). The test progress screen 287 can also include a stop command allowing the user to stop or cancel the test at any point of time. The stop command can further direct the user to the homepage or any other screen. Like the first physical test, the fitness application may also provide corresponding exercise instructions to prepare the user for the second physical test (e.g., steps 225, 230, 235, and 240 and a skip command on each screen (e.g., 234). The fitness application may also similarly initiate and display a countdown to help the user prepare his or her pace for the second physical test (e.g., step 255). The fitness application may also similarly present a first and second exertion level capture screen in the respective step after selecting the second test command (e.g., step 245 and 265). The fitness application may also similarly measure the user's heart rate, determine a pmVO2 using the measured heart rate, and assess the user's fitness level using the determined pmVO2 and other individuals health information. Accordingly, features discussed with respect to the first physical test above equally applies to the send physical test. The determined fitness level 294 and results of performing the second physical test 296 are shown in a result screen 292 (step 290). The fitness application can further provide tips to improve the results 296.

In one embodiment, the second test is a walking diagnostic test. The test requires the user to walk for a predetermined distance. The determination of pmVO2 rinsing the walking diagnostic test involves only the predetermined distance, the time spent to complete the predetermined distance, and the heart rate measured at completion of the walk. The fitness application or wearable device measures the user's heart rate after the test and the measured heart rate is used in determining pmVO2. Before initiating the test, the fitness application asks the user to wear the device 105 so that the user's heart rate before and after the test can be measured, even though only the slier measurement is used in determining pmVO2. In some embodiments, the before measurement, the after measurement, or both measurements may also be considered in determining pmVO2. The fitness application may require the user wearing the device or the heart rate measurement in order to run the test. The user's age and gender, in conjunction with the pmVO2, may be used to categorize the user into a fitness level. Preferably, the determination of the user's (fitness category is based on only the predetermined distance, the time spent to complete the predetermined distance, the measured heart rate at completion of the walk, the user's age and gender and nothing else.

The fitness application also provides a lock functionality or a lock command 202 as shown in FIG. 2H. The lock command 202 is supplied in the test progress screen which can be either screen 262 or 237 (step 211). The user can activate or click the lock command 202 to lock the test progress screen or GUI. In the locked screen 223, the fitness application continues to receive and display the live data (e.g., distance and time information) in the test progress screen and the stop command 203 is deactivated or locked to prevent the user from stopping or cancelling the test (step 221) in other words, the test cannot be stopped or cancelled when the user selects the stop command 203. The stop command 203 may have a different graphical representation or color to show the lock status aver it is locked. The lock command 202 may disappear after the stop command 203 is locked. The user may deactivate or unlock the locked stop command 203 by tapping the locked stop command 203 with a finger and holding the locked stop command 203 with the firmer for a period of time (step 231). The amount of time to unlock the stop command 203 may be an amount of time required for a color bar to completely fill up. The color bar may be positioned around the perimeter of the locked stop command 203 (the graphical representation of the locked stop commands and the fill-up speed can be determined by the fitness application. The user may also deactivate or unlock the locked stop command 203 via other methods. The lock command 202 can also be available in other screens if necessary.

Figure 3:
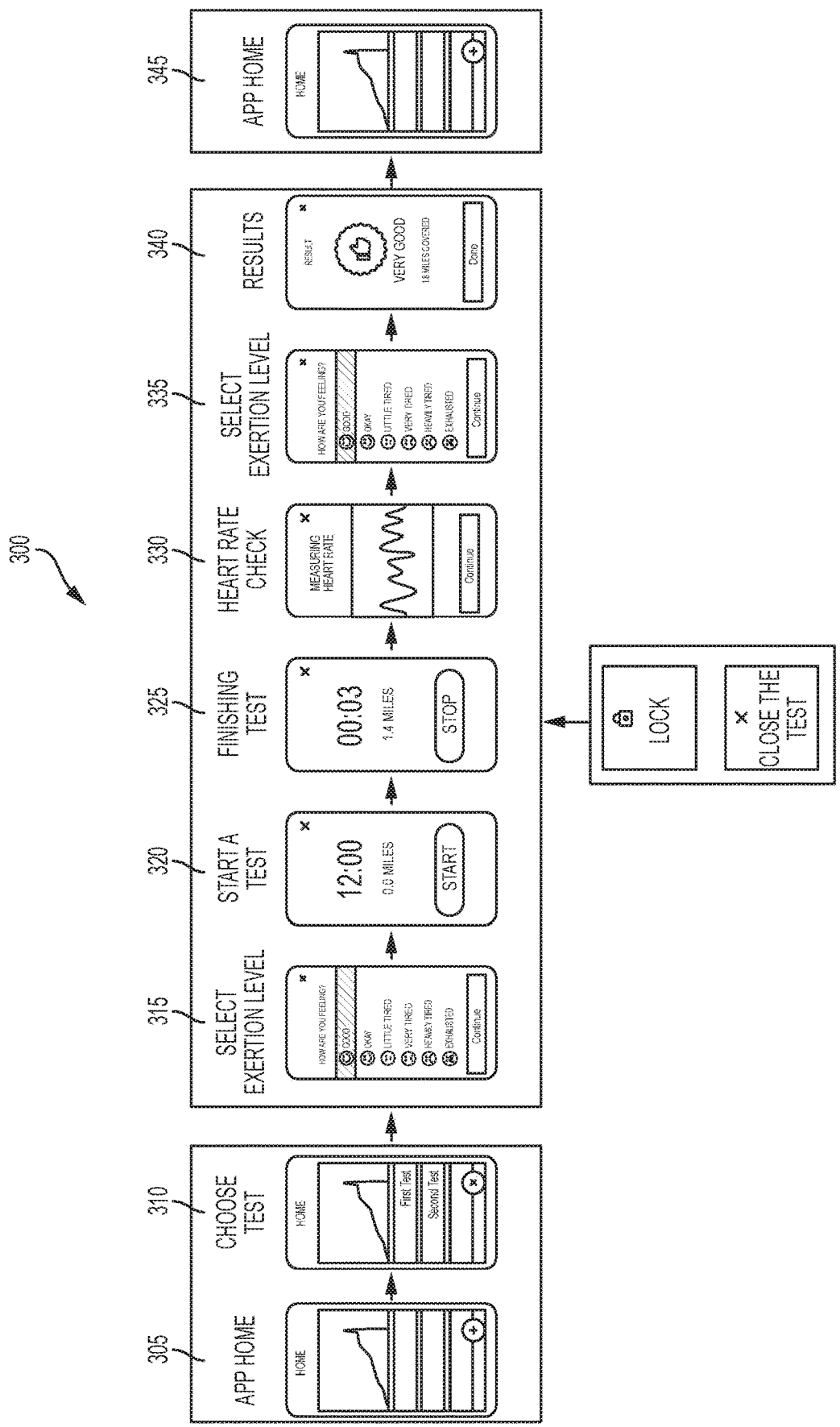
FIG. 3 depicts another illustrative flow process of the fitness application m accordance with some embodiments of the invention.

FIG. 3 depicts another illustrative flow process 300 of the fitness application in accordance with some embodiments of the invention. FIG. 3 essentially describes the flow process in FIGS. 2A-2H in one page. The flow process 300 starts with providing a test command (step 305). After selecting the test command, the user can select either the first test or the second test to proceed (step 310). An exertion level capture screen is then displayed asking the user to select his or her current exertion level (step 315). Subsequently, a test screen with a command to start the selected test is shown (step 320). The fitness application can initiate a countdown to help the user prepare his or her pace and then begin measuring the user's performance (e.g., time and/or distance) alter the start command is clicked (step 325). User's performance or progress is shown in real-time, and the test can be stopped at any time by selecting a stop command provided in the test progress screen. The same screen can also provide a command allowing the user to lock the test progress screen from accidentally cancelling the test. The fitness application can notify the user after the test is completed (e.g., after the predetermined time period is expired or the user has completed the determined distance) by sound and/or vibration (such notification can also be provided when the countdown expires). The user s heart rate is then measured and communicated to the user (step 330). Afterwards, the fitness application displays a second exertion level capture screen asking the user to select his or her current exertion level (step 335). Using the selected test, selected exertion levels, measured heart rate, and/or other information (e.g., entered user weight, height, sex, age, and other individual's health information, etc.), the fitness application then determines a fitness level of the user and displays it in a result screen (step 340). The test just performed or the latest test performed by the user and the corresponding fitness level are then saved and accessible from a screen (or home screen) containing historical tests and corresponding fitness levels. The tests and fitness levels on the screen may be sorted chronologically. The latest test and result may be shown in the top of the screen or above any other past tests and fitness levels (step 345).

The details of each step can be understood from earlier discussion. The user can use the fitness application to perform a physical test or determine a fitness level at any time he or she wishes. The fitness application may also be implemented to require the user to perform a physical nest or conduct a fitness level determination at a certain time or at a certain frequency.

Figure 4:
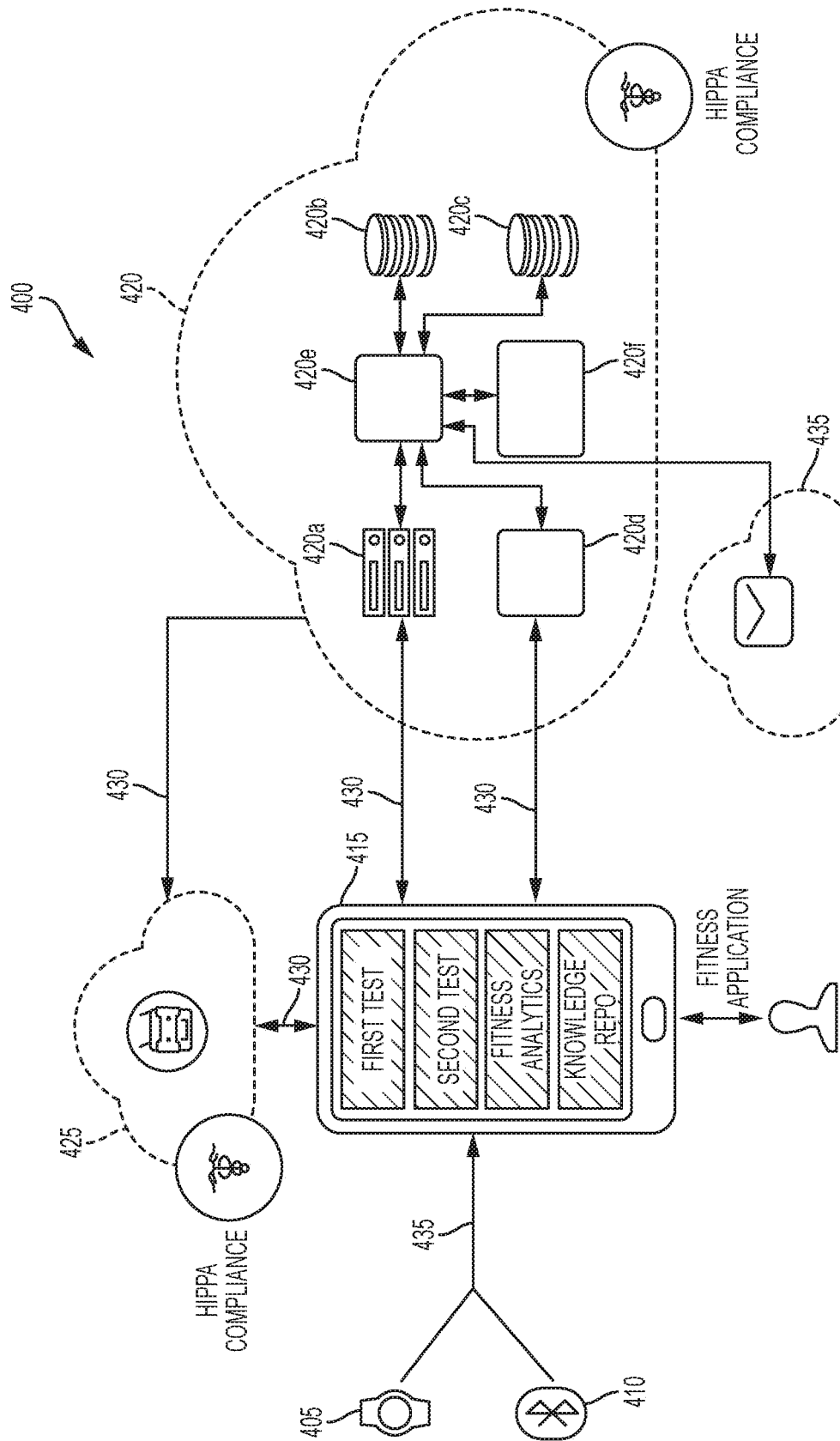
FIG. 4 depicts an illustrative system for determining physical fitness in accordance with some embodiments of the present invention.

FIG. 4 depicts an illustrative system 400 for determining physical fitness in accordance with some embodiments of the invention In addition to wearable devices (e.g., wrist-worn device 405 and chest-worn device 410 and the mobile device 415, the system 400 further comprises a management system 420 and an artificial intelligence system 425. The management systems 420 and the artificial intelligence system 425 may communicate with the mobile device 415 and with each other over a network 430 established by the protocols or wires discussed earlier. Each system includes a transmitter, receiver, or transceiver that is configured to support such protocols and/or wires. The network 430 generally has a communication range (e.g., cellular network) that is longer than the communication range of the network 435 (e.g., Bluetooth). The network 430 is secured and compliant with REpresentational State Transfer (REST) standard. Application programming interface (API) of the management system 420 is developed based on the REST architecture. Web services provided by the management system 420 are also implemented based on the REST architecture. In REST architecture, a REST server provides resources and allows a REST client to access the provided resources. Each resource is identified by URIs/Global IDs. REST uses various representations to represent resources such as Text, JSON and XML ISON.

Systems 420, 425 may be Cloud-based systems. In some embodiments, systems 420, 425 may be implemented on the same system (e.g., the artificial intelligence system is part of the management system or vice versa). A system and its subsystems can be hardware or software-based or a combination thereof. Each system and subsystem can be implemented in a separate computer system or on a single computer system. In the former implementation, the computer system of each system and subsystem includes its own processor, memory (transient and non-transient), and other electronic components to execute its corresponding functions. In the latter implementation, the computer system includes processor, memory (transient and neat-transient), and other electronic components that are configured to establish each system and subsystem and execute their corresponding functions (the same processor and memory establish each system and subsystem and execute their corresponding functions). Detail description of a computer system is described below In some embodiments, if desired, either or both systems 420, 425 or a portion thereof may be implemented on the mobile device 415. In this situation, the substantive functions of the system implemented on the mobile device 415 are performed on the mobile device 415 and that system can receive updates or other relevant information via the network 430. In general, the present description implements systems 420 and 425 separate from the user's mobile device on servers (e.g., cloud servers) connected to users or other systems via a network such as the Internet.

The management system 420 may comprise an authentication subsystem 420a, a first subsystem or database 420b configured to store authentication data, a second subsystem or database 420c configured to store health information of a plurality of individuals, a middleware subsystem 420d configured to manage communications and data from and to mobile devices, a central subsystem 420e configured to determine a user fitness level and control operations of other subsystems, and analytics subsystem 420f configured to document and report computer system errors. A management system comprising one or more of these subsystems is also contemplated. For example, the system 420 may comprise the authentication subsystem 420a, the second database 420c, the middleware subsystem 420d, and the assessment subsystem 420e with the remaining subsystems being optional In some embodiments, the assessment subsystem 420e can be implemented on the mobile device 415 and the assessment subsystem 420e can communicate with the second database 420c to obtain the necessary health information and update the second database 420c with the fitness level determined on the mobile device. The management system 420 or one or more of the subsystems can be coded using C, Objective-C, Java, JavaScript, Ruby, Pert, Python, Shell, PHP, Node.js or other programming language. Preferably, the system or subsystem is programmed using Node.js allows development of I/O for intensive web applications such as video streaming, site, singe-page applications, and other web applications. The management system 420 can communicate with a notification system 435 such tis art email server over a network 415 (which may be based on the protocols or wires described before) that sends notifications to different individuals and entities. Notification may include health information (e.g., current and past fitness levels and tips to improve fitness levels) of the user, health information of other individuals, operating status of the management system 420, and computer errors occurred on the subsystems. The different individuals and entities may include health insurance provider, medical professionals, fitness application users, software and computer system developers, and other individuals and entities.

The authentication subsystem 420a provides a login interface once a connection between the mobile device 415 and the management system 420 is created. The login interface may be the first screen displayed after the fitness application is loaded. The login interface may also be displayed in other step or seen when the user wants to access or update health information stored on the management system 420. The user can enter his or her sign-in credentials from the interface through the mobile device 415, and the entered information is transmitted over the network 430 that operates on the preferred REST API protocol to the authentication subsystem 420a First time user can also create an account from the interface. User's credentials are checked with the authentication data stored in the first database 420b via the central subsystem 420e. If the entered credentials match the credentials saved in the first database 420b, two tokens (e.g., Auth Token and Refresh Token) are generated by the authentication subsystem 420a and transmitted along with a success response to the mobile device 415. The mobile device 415 (or the fitness application) stores these tokens for maintaining current communications and establishing future communications with the management system 420. After verifying the credentials, the communication is maintained by the two tokens. During the communication, the mobile device 415 may be required to send both tokens or copier of both tokens to the authentication subsystem 420a each time the mobile device 415 attempts to access a functionality provided by the central subsystem 420e or other subsystems. If one of the tokens is missing, a computer error occurs and the communication between the mobile device 415 and the management system 420 aborts. If the entered credentials do not match the credentials saved in the first database 420b, the authentication subsystem 420a communicates to the mobile device 415 that the credentials are invalid.

The two tokens are generated with an expiration time. The first token (e.g., Auth Token) may have an expiration time that is shorter than the expiration time of the second token (e.g., Refresh Token. When the mobile device (via the fitness application) sends a request to access information or a functionality provided by the health information subsystem 420, the authentication subsystem 420a first checks if the first token is expired. If it is not expired, the mobile device (or the user) is allowed to access the requested information or functionality. If it is expired, the authentication subsystem 420a then checks whether the second token is expired. If the second token is also expired, the communication between the mobile device 415 and the health information subsystem 420a is terminated. The user is forced to log out and login again. If the second token is not expired (and the first token is expired), two new tokens are generated (e.g., new Auth Token and new Refresh Token) by the authentication subsystem 420a and transmitted to the mobile device 415. The mobile device 415 then replaces the previous tokens with die new tokens and uses new to establish and maintain future communications or requests.

The authentication subsystem 420a allows users to safely access health information and conduct a fitness level determination and helps maintain separate user accounts. The authentication method may be based on OAuth protocol or other standard authentication protocol.

The first database 420b configured to store authentication data authentication data includes the first and second token. The first database 420b may be implemented based on a Redis architecture or other architecture. For example, the first database 420b may be a Redis database. A Redis database may be an in-memory data structure store that supports daub structures such as strings, hashes, lists, sets, sorted sets with range queries, bitmaps, hyperloglogs and geospatial indexes with radius queries. The in-memory data structure allows faster data access and retrieval compared to data access and retrieval from a disk. The implementation of data structures stress on memory efficiency, so data structures inside Redis will likely use less memory compared to the same data structure modeled using other high level programming languages. A Redis database supports built-in replication, Lua scripting, LRU eviction, transactions and different levels of on-disk persistence, and provides high availability via Redis Sentinel and automatic partitioning with Redis Cluster. In addition to being used as a database, a Redis database can also serve as a cache and message broker. A Redis database is a more sophisticated version of memcached, where the operations are not just based on SETs and GETS, but work with complex data types such as Lists, Sets, ordered data structures, and so forth.

The second subsystem or database 420e is configured to store health information of a plurality of individuals. The health information may include fitness results, health conditions, and fitness classifications of the individuals. Fitness results, health conditions, and fitness classifications are determined and verified through clinical trials, observational studies (e.g., longitudinal studies), physical testing, and/or other research studies. The health information may also include health insurance costs.

Fitness results may include pmVO2s. Health conditions may be health conditions associated with the pmVO2s. Health conditions may include fatigue, heartburn, impotence, low hack pain, depression, headaches, difficulty depression, illness, disease, cancer, and other medical conditions and combinations (adverse conditions). Health conditions may also be that the person has never experienced any of the above conditions and/or has not experienced any of the above conditions for a period of time such as no illness or headache for 1 year (positive conditions). Health conditions may also be mortality, morbidity, or both mortality and morbidity associated with the pmVO2s.

pmVO2s and health conditions can be determined based on data obtained through clinical trials and research studies. The clinical trials and research studies may obtain data and determine pmVO2s in manners.

Fitness classifications may be a scale provided to assign a grade to an individual's fitness based on the pmVO2 (distance- or time-based) and or associated health conditions. Fitness classifications may include two broad categories with each further including several grades. For example, one of the categories may, represent poor fitness and the other one may represent good fitness. The poor fitness category may further include a very poor, poor, and slightly poor grade. The good fitness category may further include a fair, good, and excellent grade. Each category and grade includes a threshold pmVO2 value or range (or a threshold score) that controls the assignment of a specific pmVO2 value or range (or a threshold score). The threshold pmVO2 value or range (threshold score) is determined by the central subsystem 420e using the fitness results and health conditions.

Classifications based on the pmVO2 and/or associated health conditions indicate how fit a person is compared to the plurality of individuals (or based on the health information of other individuals) in the second database 421c. For example, pmVO2 defines the individual fitness level, wherein the fitness level is known from analysis and reverse cross reference between pmVO2 and archived data specifying the healthiness of individuals (had illness or health issues). The person subject to comparison is the user (e.g., the person wears wearable device). Fitness results in the second database 420c may be determined from treadmill stress-testing. pmVO2 by time refers to a pmVO2 determined from a heart rate measured during or after an activity that requires an individual to exercise or run continuously for a fix-period of time. pmVO2 by distance refers to a pmVO2 determined from a heart rate measured during or after an activity that requires an individual to exercise or run continuously for a fixed-distance. These pmVO2s may be obtained by having a person running nonstop for a fix-period of time or a fixed-distance on a treadmill in a clinical trial or research study. The testing includes the necessary equipment to conduct physical measurements (e.g., heart rate; and convert those measurements to pmVO2s. The testing, can be performed at fitness centers, fitness spas doctor's offices, clinics, hospitals, or other locations.

The mortality or morbidity or insurance costs) of each individual and their corresponding pmVO2 value(s) have been used and verified to identify a correlation and in turn identify, establish fitness levels. The collected data, in application, has shown a clear correlation between pmVO2 and mortality/morbidity (and, establishes fitness levels, a fitness scale, depending on where an individual falls in the range with their pmVO2 value). The data have shown to contain divergence that is used to identify different grades of fitness. Mortality/morbidity can be combined with other health information that is historically collected to correlate pmVO2 with fitness or physiological health. This techniques has been found to provide a reliable predictor of individual fitness. The use of this historical data that has been verified to be accurate through clinical trails and other testing or analysis can provide an accurate fitness determination.

For example, the second database 420c may store data that defines a fitness scale. The data may store different values or ranges of pmVO2s and the health conditions associated with each pmVO2 value or range (which may include morbidity and mortality). A fitness scale can be created using this information. For example, the fitness scale can be built with the lowest 20% of the pmVO2 values assigned to the very poor (e.g., 0-20%) category of the scale because those values have the worst mortality, morbidity or health insurance costs based on the clinical trials or other studies. The fitness scale can have the next range of pmVO2 values (e.g., 21-40%) assigned to the poor category of the scale because those values have slightly better mortality, morbidity or health insurance costs compared to the values in the very poor category but still worse than the values in the fair or other better category). The fitness scale can be built in this manner until all the pmVO2 values are assigned to a category (e.g., the next range 41%-& of pmVO2 values be assigned to the fair category, the next range 01%-80% be assigned to the good category, the neat range 81%-94 be assigned to the excellent category, and the last range 95%-100% be assigned to the superior category). The user's pmVO2 is compared with the fitness scale, and the range or category to which the user's pmVO2 belongs is the user's fitness level.

The pmVO2 determination and the verification can be performed in advance before they are provided to the second database 420c. The health informations (fitness results, health conditions, fitness classifications, or a combination thereof) of each individual may be stored as individual records. These individual records serve as an archive and can be used for comparison with the pmVO2 determined by the wearable device and/or mobile device.

The individual records can be categorized by age (e.g., at 5 year increment), gender, or other characteristic. In some embodiments, the second database 420e can store medical records of individuals and the central subsystem 420e can communicate with the second database 4210 to obtain the fitness results, health conditions, and fitness classifications using the stored medical records.

Fitness classifications stored in the database 420c can be used by the management system 420 to assign the user (the person wearing the wearable device) a fitness grade. The pmVO2 of the user is compared to the pmVO2s in the database 420. Since each pmVO2 value or range in the database 420 can be linked to one or more health conditions, the management system 420 can determine whether the user's pmVO2 value is associated with certain conditions and select an appropriate grade based on that determination. The selected grade is then transmitted to and displayed on the user's mobile device via the fitness application.

The health information of a plurality of individuals stored in the second database 420c can be updated or constantly updated. The health information can be updated by new pmVO2 values or ranges, new health conditions associated with the new pmVO2 values or ranges, new threshold pmVO2 values or ranges, or a combination thereof. The new information can get obtained from new individuals, clinical trials, observational studies (e.g., longitudinal studies), physical testing, and/or other research studies. For example, the health information of new individuals (individuals whose health information are not in the second database 420c) can be added to the second database 420c. For another example, additional health information of the existing individuals (individuals whose health information are already in the second database 420c) can be added to the second database 420. Additional health information can include new pmVO2 values or ranges obtained from additional treadmill stress-testing conducted on after the first or original treadmill stress-testing, new health conditions observed between two treadmill stress-testing or between the first treadmill stress-testing and a subsequent treadmill stress-testing or new health conditions that were not previously reported, and other health information. The threshold pmVO2 values or ranges can also be updated accordingly based on the new information. This feature provides a live feature to the second database 420c (live database 420c).

The second database 420c is also configured to store health information of a plurality of users. The health information of the plurality of users is information obtained via the fitness application. The health information include the users' fitness results (e.g., pmVO2 values or ranges) obtained from the fitness application, exertion levels captured by the fitness application, user's weight, age, sex, and other information entered into the fitness application, and fitness levels determined by the fitness application (in conjunction with the management system 420). Each time a user performs a physical test provided by the fatness application, all the associated data are stored in the second database 420c.

The number of aforementioned individuals may be larger or significantly larger than the number of aforementioned users. The number of individuals can be on a scale of 10,000, 100,000 or other larger numbers. In some embodiments, the number of users can have a similar scale depending how the fitness application is deployed. The users and the individuals may be two different groups of people. A person (or everyone) in the user group may not be a person in the individual group, and vice versa. In some embodiments, the people in the user group and the people in the individual group can overlap.

Overtime, the second database 420c may collect and store enough pmVO2s from users and generate a fitness scale solely based on those pmVO2s. The fitness scale may also be generated based on users pmVO2s and pmVO2s obtained from clinical trials and other studies.

The second database 420c may be further configured to store other data necessary to execute the functions of the management system 420 except the tokens (e.g., data received and generated by the management system 420 except the tokens or all the data except the tokens). For example, the second database 420c may be configured to store the data stained through the first and second test, such as time, distance, pre and post heart rate measurements, and user's weight for the first test and distance, time, and user's age, gender, and weight forte second test. The second database 420c is queried by the central subsystem 420e to determine the pmVO2 The second database 420c may be implemented on a MongoDB architecture or other architecture. For example, the second database 420c may be a MongoDB database. A MongoDB database provides enterprise-grade security, automation, monitoring, and integrations with an enterprise's IT infrastructure. A MongoDB database provides a data model that can accommodate the transmission and receipt of data from the mobile device and other computer systems and subsystems. The data model can be easily modified by developers when the fitness application is modified in order to transmit and receive new information. A MongoDB database can also process a large amount of data (e.g., data associated with 100, 1000, or more individuals) and provide the most up-to-date information without the users and enterprise sensing the delay A MongoDB database can also replicate large amount of data to computer systems, subsystems, and devices across different geographical regions in a consistent manner and in realtime. Instead of using tables and rows as in relational databases, a MongoDB database is built on an architecture of collections and documents. Documents comprise sets of key-value pairs and are the basic unit of data in the MongoDB database. Collections contain sets of documents and function as the equivalent of relational database tables A MongoDB database supports dynamic schema design, allowing the documents in a collection to have different fields and structures. A MongoDB database uses a document storage and data interchange format milled BSON, which provides a binary representation of JSON-like documents. A MongoDB database has an automatic sharing function that enables data in a collection to be distributed across multiple systems for horizontal scalability as data volumes increase.

The central subsystem 420e is configured to determine a user fitness level. The central subsystem 420e determines a fitness level by analyzing the pmVO2 value received from the mobile device in view of the health information stored in the second database 420c, in one embodiment, the analysis includes comparing the pmVO2 value received from the mobile device with the pmVO2 values or ranges stored in the second database, finding the closest pmVO2 value or range, and assigning the pmVO2 value from the mobile device a fitness classification based on the closest pmVO2 value or range. For example, a pmVO2 value of D is received from the mobile device. The central subsystem 420e finds that D falls between a pmVO2 range of C to E in the second database 420c. Since the pmVO2 rime of C to E corresponds to an excellent grade on the scale, the pmVO2 value from the mobile device is assigned an excellent fitness level and the assigned fitness level is transmitted to the mobile device.

In another embodiment, the analysis includes comparing the pmVO2 value received from the mobile device with the pmVO2 values or ranges stored in the second database, finding all the closest pmVO2 values or ranges, determining the health conditions associated with the closest. pmVO2 values or ranges, and assigning the pmVO2 value from the mobile device a fitness classification based on the determined the health conditions. For example, a pmVO2 value of L is received from the mobile device. The central subsystem 420e finds that L−1 and L+1 are closest to L and then determines the health conditions associated with L−1 and L+1. For instance, the health condition associated with L−1 may include headache once a week and the health conditions associated with L+1 may include fever once a month. Each of these conditions may include a score, and the central subsystem 420e can determine the total or an average score for these conditions. The score is then compared to the scores on the fitness scale to assign a fitness level to the pmVO2 value of L received horn the mobile device. If the same pmVO2 value (L') exits on the second database 420c, then the health conditions of that value L' can be used to determine the fitness level in some embodiments, the closest pmVO2 values can include the same pmVO2 value U and the next closest pmVO2 values such as L−1 and L+1. The pmVO2 values L−1 and L+1 can be narrowed, broadened, or otherwise adjusted.

Preferably, the fitness level determination or the analysis conducted by the management system 420 consists of or consists essentially of the use pmVO2 (or information representative of pmVO2) as the determinator. In other words, the management system 420 only requires pmVO2 or information representative of pmVO2 (other than user ID, password, and other general or bask information such as age or gender) in order to make or initiate a fitness determination. The input to or the information received by the management system 420 can consist of or consist essentially of pmVO2 for this purpose. Also preferably, the fatness information used by the management system to identify, monitor, message, and classify the subset of individuals (described below) can consist of or consist essentially of pmVO2 (the pmVO2 measurement from testing using app or corresponding fitness level from pmVO2 test measurement). Relying solely or primarily only on this measurement is simpler, quicker, more efficient, and easier for the implementation of the system and can also achieve high user engagement and adherence. Including many different physiological measurement (heart rate, blood pressure, etc.) or individual characteristics and related views/interfaces may be overwhelming and complicated both from a system and user perspective. Other implementations are contemplated such as using an alternative physiological (other pmVO2) measurement(s).

The assigned fitness level is stores) on the user's account on the management system 420 or the second database 420*e*. Since the health information in the second database 420 can be updated or constantly updated, the same pmVO2 value from the mobile device may be assigned a different fitness level in a different test (live central subsystem or live database). The fitness level determination occurs while the communication is maintained between the mobile devices and the management system 420 via the authentication subsystem 420*a*. The central subsystem 420*e* can update the threshold pmVO2s or scores based on the new information received front the users and the new information for the individuals.

In some embodiments, the determination of fitness level can further consider the age, sec, weight, or other information the user. For example, the central subsystem 420*e* can compare the pmVO2 of the user with the pmVO2s of the individuals who have the same or similar age, sex, weight, or a combination thereof. The determination of fitness level can further consider healthcare cost information associated with the pmVO2s of the individuals. For example, a pmVO2 value or range in the second database may show that the respective individual(s) has a higher healthcare cost because the health conditions of that individual required the individual to see a doctor and the individual cannot recover by simply resting at home or buying over-the-counter medicines. The higher healthcare cost may also due to the user or individual's age. Therefore, the determined fitness level tan also indicate whether the user is likely or unlikely to incur a high (or low) healthcare cost. The grade very poor may indicate the highest healthcare cost whereas the grade excellent may indicate the lowest healthcare cost.

As discussed above, in connection with some embodiments, the pmVO2 obtained from the mobile device or fitness application may be the only information needed from the user in order to provide an accurate and verified determination of the user's fitness and the associated healthcare cost. The management system 420 may be oriented to require only pmVO2 data in order to calculate the user's fitness.

The middleware subsystem 420*d* is configured to manage communications and data between mobile devices and the second database 420*b*. The middleware subsystem 420*d* is also configured to facilitate user authentication and validate and check headers and timestamps in packets. The analytics subsystem 420*f* is configured to document and report computer system errors. The analytics subsystem 4201 allows developers to monitor and fix crashes in real time and improve user experience. The analytics subsystem 420*f* can detect errors automatically without users providing feedback. The analytics subsystem 4201 also saves a state or condition of the management system 420 (or a subsystem) from time to time. Through the saved states, the analytics subsystem 4201 can return the management system 420 (or the subsystem) to a previous saved state. The analytics subsystem 420*f* may be based on Sentry technology or other technology. Sentry is an error tracking technology helps developers monitor and fix crashes in real time. Sentry includes features to help developers identify and debug errors and to give developers information to decide when to fix or roll back. Sentry may reproduce errors without user feedbacks. Sentry error monitoring includes each bug's history of events and actions. Sentry involves Raven.js which is an official browser JavaScript client. It automatically reports uncaught. JavaScript exceptions triggered from a browser environment, and provides a rich API for reporting developers or systems errors.

The notification system 435 is configured to notify developers of the computer system errors. The notification system may be built on SendGrid technology or similar technology. SendGrid technology involves a cloud-based SMTP provider that allows the management system 420 or its subsystem to send emails to without having the management system 420 to maintain email servers. The emails may be sent to developer's email associated with the management system 420 or developer's personal email. SendGrid may manage all of the technical details, from scaling the infrastructure to ISP outreach and reputation monitoring to whitelist services a real time analytics. In some embodiments, the notification system 435 can also be configured to notify users, doctors, and other persons that the management system 420 is experiencing a technical problem. Notification may also be provided in other forms such as text messages, voicemails, etc.

The AI system 425 is configured to operate in conjunction with the health information subsystem 420. In some embodiments, the AI system 425 may be implemented as part of the health information subsystem 420 or the fitness application. The AI system 425 provides a natural language interface or chatbot that is directed to improve the integration and effectiveness of the fitness application and the health information subsystem 420. The AI system 425 is a computer system configured to monitor the user's fitness levels, other individuals' health information and the threshold pmVO2s or scores, inquire the user to supply additional information (e.g., converse in a natural language to obtain information), and provide suggestions based on the monitoring and inquires to improve the user's fitness level. The computer system is built and programmed in manner to mimic cognitive functions that humans associate with other human minds, such as learning (e.g., learning the user's fitness levels, other individuals' health information, etc.) and problem solving (e.g., providing suggestions). The computer system includes machine learning or neural network technology to implement and improve these cognitive functions. In this caste the computer system can be configured to mimic cognitive functions of a medical doctor, fitness trainer, or other professionals. The AI can be configured to communicate in way that mimic these roles. As such, the computer system can make the same or similar decisions or suggestions as medical doctors, fitness trainers, or other professionals based on the same information. In particular, the computer system can make the same or similar decisions or suggestions as medical doctors, fitness trainers, or other professionals would have for the purpose of moving the user from a lower fitness category/grade to a higher r fitness category/grade. As it would be understood the AI system is configured to carry a natural language conversation with the user via the chat. The system has an AI engine that generates the conversation and carries the system objective based on underlying knowledge saved in the system. For example, the AI system generates suggestions that may be tailored to encourage users to move to the next fitness level, and not necessarily directing people to achieve the excellent or heat fitness level.

In one embodiment, the AI system and the associated features such as chatbot and focused messaging or suggestions for moving the user to the next grade can be optional. The operation of the fitness system 400 may involve some or all of the devices or systems shown in FIG. 4 except the AI system 425. In this embodiment, the management system 420 can be configured to receive a roster of individuals from an enterprise computer. These individuals are authorized to use the fitness application and access the management system 420. These individuals may be determined by the entity or person with which the individuals have a relationship and be input into the enterprise computer by the entity or person. The individuals may be provided with user identification information or login information that can be used to access the fitness application and the management system 420 by the entity or person. User identification information or login information can also be provided by the management system 420 to the mobile devices of the individuals once the list of authorized users is received from the enterprise computer. The user identification intimation, login information, or other verification information may be stored in the database 420b for verification or comparison with the login information provided by the individual. In some embodiments, the individuals can create their login information but the fitness application or the management system may require an authentication before the individual can do so, such as requiring the person to provide his social security number, birthday or other information. Only individual whose personal or authentication information appears on the roster or is stored in database 420b can be allowed to create their login information and access the fitness application and fitness system 400.

The management system 420 can also be configured to collect and aggregate the pmVO2 or information representative of pmVO2 of one or more authorized users in the database and then remove information identifying of those individuals. In this way, the management system 420 is configured to store pmVO2 or information representative of pmVO2 without knowing the identity of those individuals or anonymously. The saved anonymous data can be used to establish or update the Fitness scale or be used for other purposes. The management system is further configured to determine a grade using the collected pmVO2 or information representative of pmVO2 and the fitness scale (described above) to classify the one or more authorized users. The above features can also be incorporated into a fitness system 400 that includes the AI system 425, and be reinforced by or combined with the features provided by the AI system 425.

For example, there may not be a significant change in a user's physical measurement, but the same or similar result (e.g., pmVO2) may lead to a lower fitness level because there is an update or new information received) that is enough to modify the threshold pmVO2s or scores. The previous pmVO2 obtained from the user classified him or her a fair grade. The same or similar pmVO2 obtained from a current test may classify the user a slightly poor grade.

Depending on the application (described below) of the fitness system 400, the downgrade may have a negative consequence such as a significantly higher health insurance premium or significantly higher healthcare cost (e.g., because the doctor needs to perform a substantial or additional medical tests). The suggestions may also be tailored to move the user to other levels (e.g., from very poor to poor, fair to good, etc.) or one level by one level. Until the desired fitness level is achieved. The suggestions and inquiries can vary according to changes or updates made to the second database so that the fitness application can provide a personal and measured change to help the user move into a higher grade. This way, the user knows how much or how little he or she should be exercising in order to achieve a better classification For example, the AI system 425 may suggest "you should run at least 200 meters a day" or "you should consume an extra W milligrams of vitamin A a day" in an audible form. Inquiries asking the user to supply additional information may be questions such as "how many times did you exercise this week?" "How long did you exercise each time?" "What was the type of exercise," and so forth.

Through the chatbot, the user can speak or type to interact with the AI system 425. The chatbot can be configured to receive audio input, detect speech, transcribe the speech into text, process the text to understand the speech, and perform functions specified in the speech or communicate the message in the speech. The chatbot can also be configured to receive text input, process the text, and perform functions specified in the text or communicate the message in the text. The chatbot can respond via audio or text. The chatbot can be configured to convert analysis results by the AI system 425 into text, and present the textual results and/or read the textual results in audio to the user. The chatbot using the AI is configured to simulate human interaction via messages with the user of the device such as the chatbot acting as a role of a coach. The analysis results are results the AI system 423 obtains after analyzing the health information of the user and the individuals in the second database and other information in the central subsystem. The chatbot may reproduce the results in textual form only without audio. These configurations allow the AI system 425 to receive audio and/or textual input from the user and operate according those commands and to provide the appropriate suggestions and inquiries in an audible (e.g. speech), textual, and/or visual form. The chatbot can converse with the user using a synthesized voice (text to speech) or recorded voice. The user and the chatbot can communicate in audio or text back and forth to receive answers, suggestions and other information provided by the AI system 425 in real time. In other words, the chatbot can interpret the users input to infer the user's intent, translate the inferred intent into actionable tasks and parameters, execute operations or deploy services to perform the tasks, and produce output that is intelligible to the user. The AI system 425 can analyze the health information of the user and the individuals in the second database and other information in the central subsystem and translate the analysis into required actions on the part of the user and required answers from the user. The chatbot can communicate action items and questions to the user in an audible (e.g. speech), textual, and/or visual form. The chatbot serves an interface between the user and the AI system 42S. The chatbot can be accessible from the fitness application. The chatbot can also accessible without the user opening the fitness application. For example, the user can speak to and/or text with the chatbot without opening the fitness application. The management system can also communicate with the user without the user opening the fitness application (via the chatbot). The chatbot is typically configured to be a text messaging type of service.

For example, user identification or mobile device information such as a telephone number is saved in the chatbot software or management system. A separate instant messaging application such as WhatsApp or a resident text messaging (e.g., SMS) is implemented or used by the AI system and chatbot to interact with the individual users without the user opening or even running the fitness application on the mobile device. This can establish a separate and distinct communication channel with each user. This is not necessarily a notification because the user is provided a direct interface (e.g., displays an on-screen area that permits the user to enter a chat message and select to send from the screen) to respond to messages.

In preferred embodiments, the chatbot software is integrated into a company's enterprise messaging platform. A module for the chatbot software would be configured and established as a presence on the enterprise messaging platform of the company. This can for example involve creating an ID and profile for the chatbot on the enterprise platform and providing the chatbot with communications access on the enterprise messaging platform. The chatbot would be able to communicate with employees and use the fitness system related software and data to send messages to the company's enterprise messaging platform to carry its desired functionality. This messaging can be performed without the employee/user using or running their mobile fitness app of even being on their mobile devices. Not running the software means that the software is not running in the user interface on the mobile device or in the background. Examples of enterprise messaging platforms include Skype for business, Slack, Facebook Messenger, and sometimes SMS. Messaging platforms can also be other platforms that are not specifically described herein. Messaging platforms that are developed hereafter are also contemplated. An enterprise messaging platform is typically configured to be accessible by the employees of the company by using security measures such login credentials or VPN connection.

Suggestions can be provided on the result screen (FIG. 2E, 279) or on a separate screen after the result screen. Suggestions can provided when the determined fitness level (FIG. 2E, 277) is in the poor fitness category (one of the two broad categories, the soar one being good fitness category). Suggestions can help the user move into the good fitness category. Suggestions can be provided when the determined fitness level (FIG. 2E, 277) is in the good fitness category. In either situation, the AI system 425 can help the user move from a lower grade to a higher grade (e.g., very poor to poor, or good to excellent). Suggestions can also be provided in other screen or at other time. For example, upon selecting the test command 222 or one of the rest commands 223 or 224 in FIG. 2B, the AI system 425 may recommend, via the chatbot, walking for 10 minutes before performing the selected run test, that the next test should be performed on a later date, or other actions. The AI system 425 may also provide recommendations, via the chatbot, from time to time when the fitness application is running behind art operating system (e.g., through the notification bar of the mobile device and the display of the mobile device is showing the desktop or a screen of another apps. The fitness application may also provide a dedicated command to initiate the suggestion function. The AI system 425 can also inquire the user, via the chatbot, to supply additional information (which may be user weight or other information mentioned earlier in the application or information in addition to those information) that would be used in the determination of the fitness level. The inquiry can occur at or between any of the screens in FIGS. 2A-2H. The inquiry can also occur from time to time when the fitness application is running behind an operating system.

In some embodiments, the chatbot may also be configured to operate the fitness application. For example, the user can speak to the chatbot by saying "fitness application" in order to launch the fitness application. The user then can say "test command" or "first test command" in order to snake a test selection. The user can also say "result" in order to access the user's previous determined fitness levels. The chatbot can read previous determined fitness levels, the type of test performed, and the date and time on which the test was performed to the user. In other words, the user can voice control the fitness application through the chatbot.

Preferably, the management system 420 and the AI system 425 and their communication network 430 are compliant with Health Insurance Portability and Accountability Act (HIPAA) to safe card the user and individual's privacy and health information.

The system 400 for determining physical fitness has a wide range of applications In one application, the system can be implemented to be a service for an employer to enroll its employees in a health insurance plan. The employer instructs their employees to download and install the fitness application and may supply them the wearable devices. An ID number and account can be provided for each employee so that the transmission of the employee's personal information and health information is anonymous and confidential (through the authentication subsystem). The fitness application would send the test results to the management system and the management system would issue a grade to the user. The management system receives and stores health information of the users and individuals. The employer can have a relationship with a health insurance company, and the information stored on the management system can be provided to the health insurance company. The health insurance company and/or employer could use the information in revising health insurance premiums, tracking individual fitness levels, or taking related actions. There is no accurate and reliable way of tackling, predicting, or improving health insurance costs and premiums at an enterprise level. Different people will require different health or insurance needs but the level of predictability is uncertain. By using this integrated technology, the employer and insurance company can accurately determine (or predict) this information by scientifically accurate and reliable ways that involve determining and tracking fitness level of individuals and also operate or track to accomplish changes in physical change. For example, each of the fitness levels or grades may be assigned a corresponding data value (e.g., a risk profile value, health insurance premium such as vary poor: $1000, poor: $800, slightly poor $600, fair: $400, good: $200, excellent: $50). Each grade in the good fitness category (e.g., fair, good, excellent) has a premium or risk profile value lower than each grade in the poor fitness category (e.g., very poor, poor, slightly poor).

For example, the management system can be configured to communicate with an enterprise computer of an entity to receive a roster of individuals employed by the entity. The roster may include a list of individuals identified by their employee ID numbers or other codes to maintain anonymity. If desired, a list is transmitted that includes identities of employees on the employees roster (e.g., their name or their email address) and the system can use a technique such as verifying their email address against the domain names of the company to verify that they are valid users. The individuals are instructed to download the fitness application on their mobile devices. The entity may supply them the wearable devices or they may use their own wearable devices. The management system is configured to monitor fitness grades of each individual and their activity or interaction with the chatbot. This can involve active monitoring on a regular and continuous basis such as daily, hourly, or based on predetermined timing threshold (e.g., no activity reported/saved or no messages from the user in the last 12 hours). The management system can be configured to use the information communicated in a chat (involving each user) for assessing the next action or communication by the system (e.g., determines if the communication includes a persistent health problem such as a stomach ache). The information in the chat can be loped in a database and made available to a third party for examination such as a doctor (the information can if desired be filtered to extract relevant details for the third party). The management system can identify a subset of individuals that have a fitness grade that impacts a predicted healthiness of the individuals in the roster as a whole set. A fitness grade that impacts a predicted healthiness of the individuals in the roster as a whole may be a fitness grade in the poor fitness category. In other words, the management system can identify a subset of individuals that have a fitness grade in the poor fitness category and that the remaining individuals have a fitness grade in the good fitness category. A fitness grade in the poor fitness category can impact a predicted healthiness of the individuals in the roster such a grade is generally associated with adverse health conditions (and can pose different front of risk or impact to the enterprise, the individual's employer). The management system can identify those individuals and focus the operation of the system to move them to a higher fitness grade or into the good fitness category its order to improve those individuals fitness and/or lower their risk profile value.

The management system can be configured to communicate with other computers to receive rosters of individuals. For example, the computer may be an enterprise computer of a hospital or clinic that provides medical and surgical treatment to the individuals (patients), government that conducts medical testing on the individuals, an insurance company that screens the individuals (e.g., life or health insurance candidates) or has accepted the individuals (e.g., life or health insurance members). The individuals can be other group of people and be associated with other entities in other relationships.

Once those individuals are identified, the management system can send an alert to the enterprise computer notifying the employer of such situations, if desired. The alert may include the number of individuals in the subset and the employee ID numbers of those individuals for some other user identification). The AI system can then target those individuals and provide the corresponding suggestions using information in the second database to (e.g., using natural language dialogue generated by the chatbot and AI) and the central subsystem. The management system can transmit messages containing the corresponding suggestions to each of the individuals in the subset via the chatbot. After the transmission, the management system can monitor those individuals' activities and fitness via the chatbot and fitness application. Based on the monitoring, the management system can classify one car more individuals in the subset that originally have a fitness grade that impacts a predicted healthiness to a higher fitness grade (or into the good fitness category). For example, it can focus on moving a subset of individuals in an average grade level that are close to the threshold for the next grade level to move them to the next grade level. The suggestion or suggestions can include one or more actions or action items suggested to be completed by the individual that can help move the individual from his or her current fitness grade to a higher fitness grade (e.g., the suggestions can have a positive impact by improving the physical condition of the user, determined when a test moderated by the fitness app is conducted by that use).

The management system monitors and updates fitness levels of individuals from the entity. The management system determines an efficient technique to manage interactions with users and achieve system objectives. The management system determines that moving a subset of users to a next fitness level (e.g., fitness category or grade) will result in benefits such as likely health cost savings and improved company productivity. The management system identifies a set of users that are relatively close to the next fitness level or simply determines that moving certain percentage of individuals in that group from their current fitness level to the next fitness level will have significant overall benefit (across groups) such as by way of significant average likely improvement in health. The management system directs the processing of the AI system and chatbot primarily or substantially to that subset of individuals in the group (enterprise employees) and applies a relatively smaller percentage (or not effort) to other individuals that do not fall within these characteristics. Based on the use of the knowledge base, AI system, and chatbot, the management system directs messaging that focuses on steps that will move an individual in that group to the next fitness level. The messaging, AI system, and knowledge base are adapted to move individuals to the next level, e.g., not to achieve ultimate fitness or to achieve a top fitness level which can be overwhelming and have a negative reaction or result and can require a significant amount of processing (manage AI dialogues) and significant transmission of chat messages over communication channels. The management system, by ways of continuous (e.g., hourly, daily, etc.) monitoring, changes the message and interactions for an individual when they reach the next level. In other words, the focus of system operations towards that individual is reduced or removed such that for example they are treated by the management system like other individuals in the group that was not the focus. The individual is removed from the identified subset that is the focus of operations and the resources of the systems are not used or are significantly reduced in correspondence with that user (now reclassified in the better fines level).

The management system is implemented using a database (e.g., second database 420c) that stores a correlation between pmVO2 measurements and healthiness of those individuals over a period of time following the pmVO2 measurement. The database identifies fitness level in accordance with the natural stratification of the healthiness and pmVO2 measurements. The management system is configured to move or adjust the threshold or range for each fitness level by receiving overtime additional pmVO2 measurement and corresponding health information. This can be from the entity based data measurements and corresponding health insurance companies for those individuals. This can be implemented continuously or at select times to adjust the fitness level thresholds and consequently, the operation of the AI system and chatbot because the fitness level information would have changed.

A related technical implementation that is advantageous and potentially different from existing systems is that the fitness application, management system, and related components are configured to operate in a different way than direction of existing systems. Conventional systems, primarily implement a fitness application on the mobile deice and are configured to have the user track and log fitness activity (e.g., running, walking, cycling, fitness class, etc.) in the application. The data from the logging activity is stored in the application (and/or on a server) including information such as calories burned. This appears to be the fundamental approach in the industry (activity tracking and logging as the foundation) over months and years a significant volume of user logging can be generated and stored. In preferred embodiments of the present invention, the application and related system is configured to have the user perform a test that measures the user's fitness level and stores a history of test information. The system reports to the user the current fitness level as a measurement. The system (e.g., the fitness application) operates substantially without or without recording or logging exercise activity. This reduces the amount of screens or modules in the fitness application (reduces size of software) and significantly reduces the amount of data that the application and/or system stores as part of providing the application to the user. This reduces the amount of interactions by the user with the application and the related amount of time and processing on the device or system. This approach make a significant conversion in the volume of data, processing, user interfaces, and historical data compared to conventional systems or approaches.

In preferred embodiments, an additional level of security is integrated into the system by, implementing the chatbot and/or AI server outside of separate from (e.g., different server that need to address each other with different network addresses), the management system. At a first level, known systems do not implement or integrate an external chatbot and/or AI system that is configured to communicate with the fitness application (chat interface in the fitness application) or through a separate chat interface application on that user's mobile device. The chatbot and/or AI server (e.g., each a different server or combined servers) are configured to communicate with central subsystem 420e and are configured to request data from databases in management system 420 by sending requests to the central subsystem 420e rather than to be able to access the databases (e.g., databases that contain personal information collected by the system such as from testing) using database commands (or not able to access by communicating with the database management software implemented on server by hiding resources). For example, the chatbot and/or AI server is configured to send predefined types of requests using BON, which are encrypted. Central subsystem 420e receives, unencrypts, and retrieves the requested data. Central subsystem 420e transmits a message using JSON (encrypted) to the chatbot and/or AI server to fulfill the request (after checking the request for authenticity, e.g., received from approved server or address). Central subsystem 420e is configured to limit access to personal information collected and stored in the database by server data that is permitted (under local rules) to be provided to those external systems.

To provide further implementation details, the fitness application is preferably configured to operate as a software application over the operating system of the mobile phone. The fitness application receives data such as raw data from the testing performed (e.g., from the watch worn by the user) and uses tags to identify the data and mobile application using the operating system to forth one or more packets in a structured throat with the tags and send the data in one or more packets to the management system 420 (e.g., to 420e). The management system receives the packet(s) and the data based on the tags is configured and stored into a database scheme in the management system. 420, and stored in a database (discussed above) in management system 420. The communications are also encrypted (and decrypted e.g., at the management system).

Figure 5:
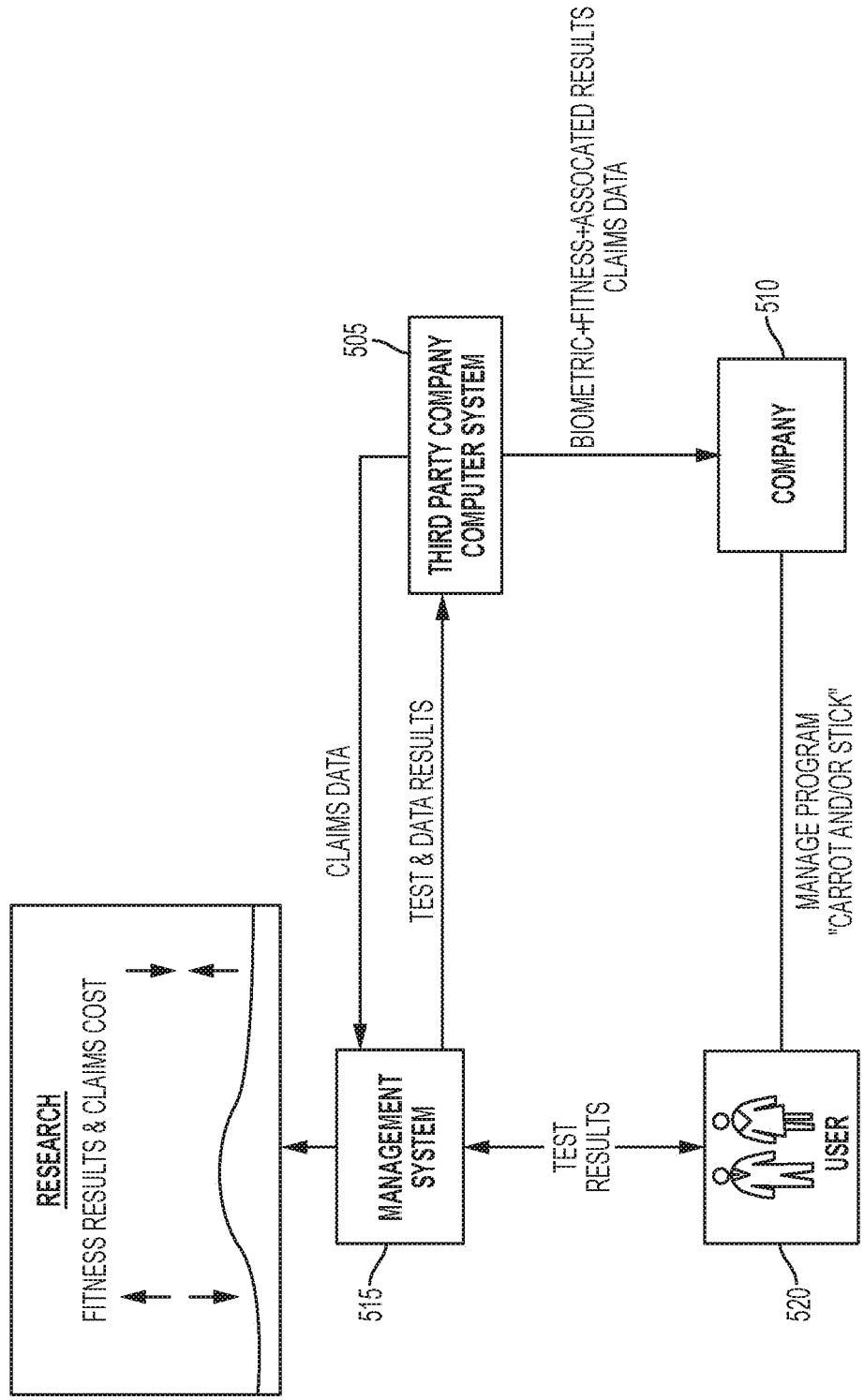
FIG. 5 depicts an illustrative third party company computer system and an illustrative enterprise computer system communicating with the management system and the mobile device in accordance with stale embodiments of the present invention.

FIG. 5 depicts an illustrative third party computer system 505 (e.g., health insurance company, life insurance company, etc.) and an illustrative enterprise computer system 510 communicating with the management system 515 and the mobile device 520 in accordance with some embodiments of the present invention. The third party computer system 505 can connect with the management system 515 to receive user test results and other data. The third party computer system 505 can provide claims data to the enterprise computer system 510 and the management system 515. The claims data tray include data based on the received test results and other data, such as health insurance premiums, doctor office visit costs, etc. based on the received test results and other data. The third party computer system 505 can also transmit the received user test results and other data upon which the claims data is based to the enterprise computer system 510. The enterprise computer system 510 and the third party company system 505 can utilize the systems 515, 520 to monitor the users' fitness levels and determine the relevant information such as healthcare costs. The management system 515 can determine the relationship between the user test results and the chants data it received. These systems may be HIPAA compliant and/or communicate using employee ID numbers or other identifications to maintain the anonymity and confidentiality of the individual's personal information and fitness/health information. For example, the systems can monitor employees using their employee IDs, identify the subset of users to be moved to the next fitness level (in order to save health costs or perform other actions) using the employee ID numbers, and direct the functionalities of the AI system and chatbot to those individuals using their employee ID numbers etc. The systems also prevent unauthorized persons from viewing or accessing employees' personal information and fitness/health information. Anonymity may be maintained in a manner such that the systems, employer, employees, and/or third party company is aware that a subset of individuals in the company need to be moved to the next fitness level and that the AI system and chatbot are interacting with those individuals to improve their fitness levels but without rowing the identities of those individuals.

The system can also be implemented to be a service for an employer to enroll its employees other purposes that are dependent on the fitness or health information of the user. For example, the employer may be a fitness center and the employees may be the trainers. The fitness center may ask the trainers to download and install the fitness application and supply them the wearable devices. The fitness center may require them to perform one of the tests periodically to stay fit because such performance is one of the employment conditions or government regulations. For instance, the condition or regulation may require that a certified trainer be capable of completing a 1 mile run in 7 minutes or obtaining a good grade after performing the test. The system can also be implemented to be a service between an entity and its customers. For example, the fitness center or trainer may ask the trainees to download and install the fitness application and supply them the wearable devices. The trainer may ask the trainees to perform one of the tests periodically to stay fit. In return, the fitness center can lower their monthly membership fee if they achieve or maintain a certain grade.

In another application, the system can be implemented to a service for a hospital or doctor to monitor their patients. The doctor instructs his or her patients to download and install the fitness application and supplies them the wearable devices. The doctor may require them to perform one of the tests periodically to stay fit. The results from performing the tests are transmitted to the hospital or doctor's computer or a third party computer on gathers the data on behalf of the hospital or doctor. The doctor can use the results from the tests or determined grades as vital signs to assess his patient's health and provide treatment. In return, the doctor can lower their medical bills or submit their insurance claims at a lower cost if they achieve or maintain a certain grade.

In another application, the system can be implemented as a service for a research protect that involves a group of individuals. The research project may be related individual's fitness or conducted for other purposes. The system can also be directed to consumers. The fitness application can be installed and used by consumers to stay lit, without having or establishing a relationship with a particular entity or professional. For example, a consumer can download the fitness application from the Google Play store and use it to monitor his or her fitness. The consumer can use the fitness application at any tune he or she wishes, and the results can be saved for his or her own record without being used for a particular purpose (e.g., for lowering health insurance premium, because the doctor told him to do so, etc.)

In another application, the system can be implemented as a service for an insurance company to titter or qualify individuals for an insurance plan or different insurance a plans, or to monitor current members (individuals who have been accepted to an insurance plan) and change their insurance plans. An insurance plan can be a health insurance plan, life insurance plan, or other insurance plan. For life insurance, the determined grade can be used as an individual factor or combined with other population data to generate an actuarial category for an individual.

The computer may be an enterprise computer of an entity that employs the individuals (employees), a hospital or clinic that provides medical and surgical treatment to the individuals (patients), government that conducts medical testing on the individuals, an insurance company that screens the individuals (e.g., life or health insurance candidates) or has accepted the individuals (e.g., life or health insurance members). The individuals can be other group of people and be associated with other entities in other relationships.

In some embodiments, the system receives and stores data, about the employees of different enterprises such as a fitness grade, age, gender, fitness activity, chat dialogue (or information derived from chat dialogue) in a database in the management system. This information can be associated with identify information for each user. The management system can be configured to aggregate and anonymize this data (strip identifications) when it is aggregated by deleting the user identity information when it is processed during the aggregation process. The management system can be configured to receive third party data from another data source such as mortality or health conditions and can be further configured to process the combination of aggregated anonymous data with the third party data and identify correlations based on divergence or convergence of data anti in response, identify different classifications.

The system can be configured to include a chat option within the fitness application (displayed in an interface window of the fitness application) on the mobile device if desired.

If desired, a point system is implemented by the system that is used to track the activity of the user and used as a basis for the AI and chatbot to generate messages. For example, a database in the management system can store information such as in a table (based on a particular knowledge base and structure) that specifies a certain number of points for different activities or situations. A user can manually enter information specifying an activity and the system can look up the corresponding points and save those points for that user. A tracking method can also be used such as by tracking a distance walked and corresponding points are saved. There can be different points for running, walking, or other activity. The points are tracked to evaluate the progress of the user and determine the type or content of suggestions or messages that should be sent to the user next. The points provide one technique for monitoring a user (and the user's progress) and adapting the operation of the system (e.g., the AI or chat) to match the user's history and frequency of activity (e.g., in recent days). The AI and chat can also track such information and engage the user m dialogue about potential reasons why the user has not been active or has changed a pattern of activity or interaction. In response to the tracking, the system can send signals such as a message that alerts the user's company about certain identified behavior such as tack of responsiveness to the messages generated by the system.

The above point system can be the point system described in the book *Aerobics* authored by Dr. Kenneth H Cooper in 1968 or in the publication *The Aerobics Program for Total Well-Being* prepared by the same scholar in 1982. Both documents are incorporated herein by reference.

The monitoring can include the content of conversation using the AI and chatbot such as tracking the time of day, the duration, how often the user communicates, the content (e.g., mood, particular health problem, etc.), and other information. The monitored or tracked information is used in the chatbot and AI.

In some embodiments, the fitness application or other element in the system stores electrocardiogram readings or measurements of each user, showing the heartbeat pattern of the user. The electrocardiogram information is used authentication by comparing heart rate data from the heart rate sensor worn by the user with the stored electrocardiogram data and the comparison providing an authentication that the actual user, associated with that device or fitness application, is being tracked or tested. The comparison may involve using a data derived from the electrocardiogram data that indicates a type of fingerprint. The electrocardiogram data can be collected and stored using different techniques or devices. This technique can provide a technical advantage in allowing the system to preterit users from cheating by having other individuals use the fitness application.

Applications to other fields are also contemplated.

The term bean raw measurement can refer to a bean rate measured by the wearable device at a particular time. The same term can refer to a peak heart rate measurement. The wearable device can monitor a users heart rate for a period of curie and record the highest rate sensed during that period of time.

Although this disclosure describes conducting heart rate measurement and using the measurement to obtain pmVO2, in some embodiments, other physical measurements (e.g., body temperature) and index or conversion (e.g., body temperature index) may be used.

The fitness application and the fitness system can be configured to provide multiple tests or more than two tests. These tests can be done by any format, such as 5 or 10 times a year. In some applications, the goal may be to measure progress in some measure of frequency, but the fitness application can be made available only once a year, or let the user use it as frequent as possible. In some embodiments, the entity or person with whom the user has a relationship could decide. The user could also have the option to select either the first or second test. The results from the test can be saved, aggregated, and tracked. Each user can select to perform any of the available tests on the application e.g., walk or run and the system would record and save the information. The system would determine pmVO2 (for walk or run, whichever selected by that use in that instance) and record the fitness grade and pmVO2 value. The system can average the results (regardless of whether a run or walk test was performed) and the result can provide information on the progress or current status of that user. The functionality that provides such flexibility to (e.g., use any of the tests) can provide better accuracy and reliable progress information.

In preferred embodiments, the fitness application and the system are configured to include little or no requirement for the user to input personal information such as health history, habits, medical history, or other lengthy questionnaires. In existing systems in this field, the systems typically include initial questionnaires that require the user to provide detailed information. This can add to the size of the mobile application on the device and make it difficult for users to use the system. The user interface displayed by the fitness application to the user preferable does not include lengthy questionnaires and substantially only involves the input displays that are illustrated herein. For example, the fitness application generates user interfaces for entering user information that consists of or consists essentially of entering login 113 and password, age, gender, weight, test connected data (see figures), activity information (manually or automatically entered information about activity), chat data, or individual combinations thereof. This can also reduce the amount of processing and data that is communicated, processed, and stored.

Counterpart method and computes-readable medium embodiments would be understood from the above and the overall disclosure. Also, broader, narrower, or different combinations of the described features are contemplated, such that, for example features can be removed or added in a broadening or narrowing way.

There are a number of technical solutions and advances that are provided by embodiments of the present invention. The embodiments or features thereof (or combinations of features) are also not routine conventional, or well-understood in the industry. The patent application is directed to the implementation of a system and its components to accomplish various objectives rather than simply being directed to an objective or idea. Specific architectures, connections, and operations are for example described.

Some illustrative technical points of note are provided without any particular priority. The system includes and integrates specialized devices such as a heart rate monitor and a mobile device (e.g., a mobile phone). Conventional fitness applications are configured to be directed to perform operations and interaction with a focus on a single user using that application. Preferred embodiments are configured to operate and focus on a group of users, a larger set of curers, and to interact with the users and make decisions based on the group (a group of data from different individuals). The system is for example configured to evaluate and selected a group within a larger group and focus the processing and operation of the system (e.g., AI and chatbot) substantially only on that subset relative to other users in that group. This is in a different direction than known conventional systems. In some embodiments, the system integrates with an enterprise server. Another unconventional aspect (relative to known systems) is that it is integrated with a chatbot and AI system. This integration can allow for the systems to communicate with the user in natural language independent of the fitness application on the mobile device (e.g., the fitness application is not running or could have been deleted). The interaction can continue with the system using the chatbot and in some embodiments, the chatbot is integrated as an entity (virtual user) or module on the company's enterprise chat systems which provides easy integration for fitness system, users and the enterprise with the system. Preferred embodiments are also configured to provide a system that is more efficient and operates quickly by for example miming the amount of messages that need to be generated by only, substantially, or substantially only focusing the tracking and the veneration and transmission of message to a subset of users that are in a particular threshold fitness scale. This reduces the amount of processing and the volume of messages that are sent by the system and communicated over a communications paths. Another aspect of note is that this system can focus on the verifiable fitness condition of each user by using a fitness scale that that is correlated to historical data that has been saved and verified. This is different from known typical conventional fitness systems because these systems do not and cannot focus on determining or using a true fitness level of the user. Another efficiency is provided by the system focusing on performing operations directed to managing a user(s) by generating communications to move to a next fitness level rather than to transmit many messages or perform related operations (or tracking) to direct all or substantially all user to read for absolute fitness. The incorporation of reasonableness reduces the amount of messaging and processing. These, their combinations, and potentially other aspects are relevant to having an appropriate understanding of embodiments of the present invention.

The system can also be integrated with other computers, systems, software, messaging platforms, technologies, and standards that are not specifically described herein or that are developed hereafter.

Technical advantage provided by the various implementations of the system and method are evident from the herein disclosure.

In one embodiment, the computer system includes a bus or other communication mechanism for communicating information, and a hardware processor coupled with bus for processing information. Hardware processor may be, for example, a general purpose microprocessor or microcontroller. The computer system also includes a main memory, such as a random access memory (RAM) or other dynamic storage device, coupled d to bus for storing information and instructions to be executed by processor. Main memory also may be used for storing temporary variables or other intermediate information during execution of instructions to be executed by processor. Such instructions, when stored in non-transitory storage media accessible to processor, render computer system into a special-purpose machine that is customized to perform the operations specified in the instructions. A computer system further includes a read only memory (ROM) or other static storage device coupled to bus for storing static information and instructions for processor. A storage device, such as a magnetic disk or optical disk, is provided and coupled to bus for storing information and instructions. If desired, a computer system may be coupled via bus to a display, such as an LCD, and LED for displaying information to a computer user, and/or an input device, including alphanumeric and other keys, is coupled to bus for communicating information and command selections to processor. Another type of user input device is cursor control, such as a mouse, a trackball, or cursor direction keys for communicating direction information and command selections to processor and for controlling cursor movement on display. This input device typically has two degrees of freedom in twee fixes, a first axis (e.g., x) and a second axis (e.g., y), that allows the device to specify positions in a plane. A computer system may implement the techniques described herein using customized hard-wired logic, one or more ASICs or FPGAs, firmware and/or program logic which in combination with the computer system causes or programs computer system be a special-purpose machine. According to one embodiment, the techniques herein are performed by computer system in response to processor executing one or more sequences of one or more instructions contained in train memory. Such instructions may be read into main memory from another storage medium, such as storage device. Execution of the sequences of instructions contained in main memory causes processor to perform the process steps described herein. In alternative embodiments, hard-wired circuitry may be used in place of or in combination with software instructions.

The term storage media as used herein refers to any non-transitory media that store data and/or instructions that cause a machine to operation in a specific fashion. Such storage media may comprise non-volatile media and/or volatile media. Non-volatile media includes; for example, optical or magnetic disks, such as storage device. Volatile media includes dynamic memory, such as main memory. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus. Transmission media can also take the form of acoustic or light waves, such as those generated during radio-wave and infra-red data communications.

Various forms of media may be involved in carrying one or more sequences of one or more instructions to processor for execution. For example, the instructions may initially be carried on a magnetic disk or solid state drive of a remote computer. The remote computer can load the instructions into its dynamic memory and send the instructions over a telephone line using a modem. A modem local to computer system can receive the data on the telephone line and use an infra-red transmitter to convert the data to an infra-red signal. An infra-red detector can receive the data carried in the infra-red signal and appropriate circuitry can place the data on bus. Bus carries the data to main memory, from which processor retrieves and executes the instructions. The instructions received by main memory may optionally be stored on storage device either before or after execution by processor.

The computer system also includes a communication interface coupled to bus. Communication interface provides a two-way data communication coupling to a network link that is connected to a local network. For example, communication interface may be an integrated services digital network (ISDN) card, cable modem, satellite modem, or a modem to provide a data communication connection to a corresponding type of telephone line. As another example, communication interface may be a local area network (LAN) card to provide a data communication connection to a compatible LAN. Wireless links may also be implemented. In any such implementation, communication interface sends and receives electrical, electromagnetic or optical signals that carry digital data streams representing various types of information.

A network link typically provides data communication through one or more networks to other data devices. For instance, network link may provide a connection through local network to a host computer or to data equipment operated by an Internet Service Provider (ISP). ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface, which carry the digital data to and from computer system, are example forms of transmission media.

A computer system can send messages and receive data, including program code, through the network(s), network link and communication interface. In the Internet example, a server might transmit a requested code for an application program through Internet, ISP, local network and communication interface.

The received code may be executed by processor as it is received: an for stored in storage device, or other non-volatile storage for later execution.

To clarify, computer based devices (which are the systems or devices discussed herein) in general are understood to include a processor, communications circuitry, transitory memory (volatile memory, such as RAM), and nontransitory memory (e.g., nonvolatile memory that stores data or software). As described above, the mobile devices, hear rate measuring devices, and GPS devices are specialized devices having certain hardware and software components. These devices and related functionality are for example integrated into the described systems. Embodiments of the invention contemplates use of the devices in a described method or in connection with a systems or subsystem that receives the data or measurements. The described systems can also be implemented on computer based devices and other hardware and software that are not specifically described herein or that are developed hereafter.

It is understood from the above description that the functionality and features of the systems, devices, or methods of embodiments of the present invention include generating and sending signals to accomplish the actions.

It should be understood that variations, clarifications, or modifications are contemplated. Applications of the technology to other fields are also contemplated.

Exemplary systems, devices, and methods are described for illustrative purposes. Further, since numerous modifications and changes will readily be apparent to those having ordinary skill in the art, it is not desired to limit the invention to the exact constructions as demonstrated in this disclosure. Accordingly, all suitable modifications and a equivalents may be resorted to falling within the scope of the invention.

Thus, for example, any sequence(s) and/or temporal order of steps of various processes or methods (or sequence of device connections or operation) that are described herein are illustrative and should not be interpreted as being restrictive. Accordingly, it should be understood that although steps of various processes or methods or connections or sequence of operations may be shown and described as being in a sequence or temporal order, but they are not necessarily limited to being carried out in any particular sequence or order. For example, the steps to such processes or methods generally may be carried out in various different sequences and orders, while still falling within the scope of the present invention. Moreover, in some discussions, it would be evident to those of ordinary skill in the art that a subsequent action, process, or feature is in response to an earlier action, process, or feature.

It is also implicit and understood that the applications or systems illustratively described herein provide computer-implemented functionality that automatically performs a process or process steps unless the description explicitly describes user intervention or manual operation.

It should be understood that claims that include fewer limitations, broader claims, such as claims without requiring a certain feature or process step in the appended claim or in the specification, clarifications to the claim elements, different combinations and alternative implementations based on the specification, or different uses, are also contemplated by the embodiments of the present invention. For example, one embodiment can be directed to the management system without inclusion of the wearable device, mobile device, or fitness application (e.g., focusing on a system interacting with mobile devices).

The words "can" or "may" are used to communicate or clarify that this is one option and others options or variations are contemplated. This is not to say that if such a word is not used, it is being communicated that this only implementation.

It should be understood that combinations of described features or steps are contemplated even it they are not described directly together or not in the same context.

The terms or words that are used herein are directed to those of ordinary skill in the art in this field of technology and the meaning of those terms or words will be understood from terminology used in that field or can be reasonably interpreted based on the plain English meaning of the words in conjunction with knowledge in this field of technology. This includes an understanding of implicit features that for example may involve multiple possibilities, but to a person of ordinary skill in the an a reasonable or primary understanding or meaning is understood.

Software can be implemented as distinct modules or software applications or can be integrated together into an overall application such as one that includes the user interface and that handles other feature for providing the functionality to the user on their device.

It is intended that the specification and examples be considered as exemplary only, with a true scope being indicated by the cairns and their equivalents.

What is claimed is:

1. A system for determining physical fitness comprising: a management system comprising a database and a central subsystem, wherein the central subsystem is configured to:
   verify whether a user attempting to use a fitness application of a mobile device configured to communicate to with the management system is an authorized user by consulting a raster from the database or an enterprise computer;
   operate with the fitness application that provides options via a user interface allowing selection of one or more physical tests,
      wherein, in response to a selection of the one or more physical tests on the fitness application, the fitness application communicates with the mobile device to receive a physical measurement from a wearable or implant device of the user;
   collect in the database predicted max lung oxygen volume max (pmV02) of information representative of pmV02 of the user determined from the one or more physical tests and remove information identifying the user so that the pmV02 or information representative of pmV02 of the user is saved in the database anonymously;
   determine a fitness grade from a fitness scale based on health information,
      wherein the health information stored in the database comprises the collected pmV02 or information representative of pmV02 and health conditions associated therewith, and
      wherein the fitness scale stored in the database comprises multiple fitness grades for classifying the user;
   collect in the database new health information comprising new pmV02 or new information representative of pmV02 of the user determined from the one or more physical tests, or new health conditions associated therewith;
   update the fitness grade based on the new health information; and
   transmit the updated fitness grade or a change of fitness grades before and after the update to the mobile device.

2. The system of claim 1, wherein the management system further includes an artificial intelligence (AI) subsystem that is configured to communicate a suggestion via a chatbot that generates a natural language message using the database and the central subsystem.

3. The system of claim 2, wherein the suggestion includes an action item to be completed by the user that can move the user to a higher fitness grade or a fitness grade desired by the user.

4. The system of claim 3, wherein the management system is further configured to identify a subset of users that have a fitness grade in the fitness scale that impacts a predicted healthiness of individuals in a roster as whole.

5. The system of claim 4, wherein the management system is further configured to generate and transmit messages containing suggestions provided by the AI subsystem to the mobile devices of a subset of users via the chatbot, wherein the management system is configured to control the operation of the AI subsystem, chatbot and related generation and transmission of the messages to be directed substantially only primarily to the subset of users relative to the other users.

6. The system of claim 5, wherein the management system is further configured to monitor level of activity and fitness grades of the subset of users via the chatbot and fitness application after transmitting the messages containing the suggestions and use the monitored information in the AI subsystem in responding to an individual user's monitored activity and generating new messages by the chatbot.

7. The system of claim 2, wherein the chatbot is configured to communicate with a user without requiring the user to open the fitness application or have it running on the mobile device.

8. The system according to claim 1, wherein the one or more physical tests are configured to be conducted at a medical facility, a fitness center, or a clinic using treadmill.

9. The system according to claim 1, wherein the fitness application is configured to instruct the wearable or implant device to conduct and transmit the measurement upon expiration of a determined period of time.

10. The system according to claim 1, wherein the fitness application is configured to instruct the wearable or implant device to conduct and transmit the measurement upon completion of a determined distance.

11. The system according to claim 1, wherein the one or more physical tests include a second physical test requiring the user to travel a distance determined by the fitness application and the total time spent by the user to complete the determined distance is measured by a timer of the system.

12. The system according to claim 1, wherein a user's health information or fitness grade in the database is configured to be accessible by a third party or transmittable to a third party's computer.

13. The system according to claim 12, wherein the third party comprises a hospital, a clinic, a fitness center, an insurance company, and an individual thereof or affiliated therewith.

14. The system according to claim 1, wherein the health information further comprises age, sex, weight, or other information the user.

15. The system according to claim 14, wherein the health information further comprises age, sex, weight, or other information the user.

16. The system according to claim 1, wherein pmV02 or information representative of pmV02 of a user is compared to pmV02 or information representative of pmV02 of an individual having the same or similar health information.

17. The system according to claim 15, wherein pmV02 or information representative of pmV02 of a user is compared to pmV02 or information representative of pmV02 of an individual having the same or similar age, sex, weight, or other information.

18. The system according to claim 1, wherein the health conditions comprise fatigue, heartburn, impotence, low back pain, depression, headaches, difficulty depression, illness, disease, cancer, or other medical conditions.

19. The system according to claim 1, wherein the health conditions comprise mortality or morbidity.

20. The system according to claim 1, further comprising a notification system that is configured to communicate with the management system that notifies individuals and entities related to the system.

* * * * *